United States Patent
Dimeo, Jr. et al.

(10) Patent No.: US 8,109,130 B2
(45) Date of Patent: Feb. 7, 2012

(54) APPARATUS AND PROCESS FOR SENSING FLUORO SPECIES IN SEMICONDUCTOR PROCESSING SYSTEMS

(75) Inventors: Frank Dimeo, Jr., Falls Church, VA (US); Philip S. H. Chen, Bethel, CT (US); Jeffrey W. Neuner, Bethel, CT (US); James Welch, Clayton, NC (US); Michele Stawasz, New Milford, CT (US); Thomas H. Baum, New Fairfield, CT (US); Mackenzie E. King, Southbury, CT (US); Ing-Shin Chen, Danbury, CT (US); Jeffrey F. Roeder, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 12/537,910

(22) Filed: Aug. 7, 2009

(65) Prior Publication Data

US 2009/0305427 A1 Dec. 10, 2009

Related U.S. Application Data

(60) Continuation of application No. 11/057,735, filed on Feb. 14, 2005, now abandoned, which is a division of application No. 10/273,036, filed on Oct. 17, 2002, now Pat. No. 7,080,545.

(51) Int. Cl.
*G01N 33/00* (2006.01)

(52) U.S. Cl. ......... 73/31.05; 73/23.2; 73/31.01; 422/83; 422/98

(58) Field of Classification Search ............. 73/23.2, 73/31.01, 31.02, 31.03, 31.05, 204.27; 422/83, 422/98
See application file for complete search history.

(56) References Cited

U.S. PATENT DOCUMENTS

| | | | | |
|---|---|---|---|---|
| 1,643,155 A | * | 9/1927 | Eisenschitz | 422/95 |
| 1,646,247 A | * | 10/1927 | Heinicke | 73/23.2 |
| 1,727,185 A | * | 9/1929 | Thornton | 73/31.05 |
| 1,798,977 A | | 3/1931 | Erickson | |
| 1,971,038 A | * | 8/1934 | Hamilton | 73/25.03 |
| 1,995,870 A | * | 3/1935 | Stone | 422/94 |
| 2,194,250 A | | 3/1940 | Turek | |

(Continued)

FOREIGN PATENT DOCUMENTS

| | | |
|---|---|---|
| GB | 636647 | 5/1950 |
| JP | 57-084342 A | 5/1982 |
| JP | 63-186136 A | 8/1988 |

(Continued)

OTHER PUBLICATIONS

Anderson, Bob, et al., "Using COO to select nitride PECVD clean cycle", "Semiconductor International", Oct. 1993.

(Continued)

*Primary Examiner* — Daniel Larkin
(74) *Attorney, Agent, or Firm* — Hultquist, PLLC; Steven J. Hultquist; Frank J. Bozzo

(57) ABSTRACT

A gas detector and process for detecting a fluorine-containing species in a gas containing same, e.g., an effluent of a semiconductor processing tool undergoing etch cleaning with HF, $NF_3$, etc. The detector in a preferred structural arrangement employs a microelectromechanical system (MEMS)-based device structure and/or a free-standing metal element that functions as a sensing component and optionally as a heat source when elevated temperature sensing is required. The free-standing metal element can be fabricated directly onto a standard chip carrier/device package so that the package becomes a platform of the detector.

22 Claims, 19 Drawing Sheets

U.S. PATENT DOCUMENTS

| | | | |
|---|---|---|---|
| 2,194,520 A * | 3/1940 | Darrah | 340/633 |
| 2,306,509 A * | 12/1942 | Talmey | 200/61.03 |
| 2,393,650 A * | 1/1946 | Metcalf | 73/23.2 |
| 2,774,652 A * | 12/1956 | Vonnegut | 436/36 |
| 2,861,450 A | 11/1958 | Ransley | |
| 3,232,712 A | 2/1966 | Stearns | |
| 3,270,232 A | 8/1966 | Bailey, Jr. et al. | |
| 3,315,245 A | 4/1967 | Johnson | |
| 3,437,511 A | 4/1969 | Hough | |
| 3,464,269 A | 9/1969 | Froger | |
| 3,478,574 A | 11/1969 | Modell | |
| 3,522,010 A | 7/1970 | Archer | |
| 3,523,408 A | 8/1970 | Rosenberg | |
| 3,550,247 A | 12/1970 | Evans et al. | |
| 3,616,677 A | 11/1971 | Oppengaard | |
| 3,676,293 A | 7/1972 | Gruber | |
| 3,764,269 A | 10/1973 | Oldham et al. | |
| 3,892,528 A | 7/1975 | Fredericks | |
| 3,975,210 A | 8/1976 | Warnock | |
| 3,999,947 A | 12/1976 | Mihara et al. | |
| 4,019,861 A | 4/1977 | Dahms | |
| 4,087,393 A | 5/1978 | Tsubuko et al. | |
| 4,087,693 A | 5/1978 | Brown et al. | |
| 4,319,000 A * | 3/1982 | Gagliani et al. | 521/189 |
| 4,338,281 A | 7/1982 | Treitinger et al. | |
| 4,358,949 A * | 11/1982 | MacFarland et al. | 73/31.03 |
| 4,367,127 A | 1/1983 | Messing et al. | |
| 4,415,877 A | 11/1983 | Takami et al. | |
| 4,447,397 A | 5/1984 | Anouchi et al. | |
| 4,480,779 A | 11/1984 | Luc | |
| 4,538,457 A * | 9/1985 | Gneiss et al. | 73/204.27 |
| 4,580,439 A | 4/1986 | Manaka | |
| 4,604,895 A * | 8/1986 | Watkins | 73/204.27 |
| 4,662,212 A | 5/1987 | Noguchi et al. | |
| 4,671,852 A | 6/1987 | Pyke | |
| 4,680,093 A | 7/1987 | Morin | |
| 4,685,325 A | 8/1987 | Warchol | |
| 4,723,438 A | 2/1988 | Adler-Golden et al. | |
| 4,728,494 A | 3/1988 | Berchtold et al. | |
| 4,829,819 A | 5/1989 | Lefteriou et al. | |
| 4,872,759 A | 10/1989 | Stich-Baumeister et al. | |
| 4,953,387 A | 9/1990 | Johnson et al. | |
| 5,017,875 A * | 5/1991 | Hori et al. | 324/446 |
| 5,055,266 A | 10/1991 | Stetter et al. | |
| 5,072,262 A | 12/1991 | Uekita et al. | |
| 5,081,869 A | 1/1992 | Hachey et al. | |
| 5,098,864 A | 3/1992 | Mahulikar | |
| 5,104,513 A | 4/1992 | Lee et al. | |
| 5,229,625 A | 7/1993 | Suzuki et al. | |
| 5,356,756 A | 10/1994 | Cavicchi et al. | |
| 5,376,255 A | 12/1994 | Gumbrecht et al. | |
| 5,380,192 A | 1/1995 | Hamos | |
| 5,387,462 A | 2/1995 | Debe | |
| 5,434,551 A | 7/1995 | Chen et al. | |
| 5,464,966 A | 11/1995 | Gaitan et al. | |
| 5,602,051 A | 2/1997 | Cronin et al. | |
| 5,605,612 A | 2/1997 | Park et al. | |
| 5,612,489 A | 3/1997 | Ragsdale et al. | |
| 5,679,576 A | 10/1997 | Kawai et al. | |
| 5,693,545 A | 12/1997 | Chung et al. | |
| 5,728,940 A * | 3/1998 | Kim et al. | 73/40.7 |
| 5,752,410 A | 5/1998 | Bernstein | |
| 5,791,983 A | 8/1998 | Robertson | |
| 5,801,070 A | 9/1998 | Zanini-Fisher et al. | |
| 5,827,947 A | 10/1998 | Miller et al. | |
| 5,827,952 A | 10/1998 | Mansure et al. | |
| 5,834,627 A | 11/1998 | Ricco et al. | |
| 5,841,017 A | 11/1998 | Baraket et al. | |
| 5,849,113 A | 12/1998 | Murakami et al. | |
| 5,885,361 A | 3/1999 | Kikuchi et al. | |
| 5,900,128 A | 5/1999 | Gumbrecht et al. | |
| 5,907,765 A | 5/1999 | Lescouzeres et al. | |
| 5,932,176 A | 8/1999 | Yannopoulos et al. | |
| 6,009,742 A | 1/2000 | Balko | |
| 6,093,308 A | 7/2000 | Lewis et al. | |
| 6,100,587 A | 8/2000 | Merchant et al. | |
| 6,106,734 A | 8/2000 | Shindo et al. | |
| 6,167,761 B1 | 1/2001 | Hanzawa et al. | |
| 6,171,378 B1 | 1/2001 | Manginell et al. | |
| 6,179,413 B1 | 1/2001 | Coulman et al. | |
| 6,196,052 B1 | 3/2001 | May et al. | |
| 6,202,472 B1 | 3/2001 | Wezurek et al. | |
| 6,202,473 B1 | 3/2001 | Stokes et al. | |
| 6,236,046 B1 | 5/2001 | Watabe et al. | |
| 6,265,222 B1 | 7/2001 | DiMeo et al. | |
| 6,274,198 B1 | 8/2001 | Dautartas | |
| 6,284,666 B1 | 9/2001 | Naeem et al. | |
| 6,321,587 B1 | 11/2001 | Laush | |
| 6,370,950 B1 | 4/2002 | Lammerink | |
| 6,383,401 B1 | 5/2002 | Labzentis et al. | |
| 6,413,923 B2 | 7/2002 | Honda et al. | |
| 6,428,713 B1 | 8/2002 | Christenson et al. | |
| 6,443,179 B1 | 9/2002 | Benavides et al. | |
| 6,444,487 B1 | 9/2002 | Boggs et al. | |
| 6,455,232 B1 | 9/2002 | Lin et al. | |
| 6,463,789 B2 | 10/2002 | Moos et al. | |
| 6,468,642 B1 | 10/2002 | Bray et al. | |
| 6,499,354 B1 | 12/2002 | Najafi et al. | |
| 6,531,858 B2 | 3/2003 | Chou et al. | |
| 6,553,335 B2 | 4/2003 | Huang et al. | |
| 6,553,354 B1 | 4/2003 | Hausner et al. | |
| 6,596,236 B2 | 7/2003 | DiMeo, Jr. et al. | |
| 6,617,175 B1 | 9/2003 | Arno | |
| 6,618,174 B2 | 9/2003 | Parker et al. | |
| 6,634,213 B1 | 10/2003 | O'Connor et al. | |
| 6,637,253 B2 | 10/2003 | Dean et al. | |
| 6,649,994 B2 | 11/2003 | Parsons | |
| 6,691,554 B2 | 2/2004 | Eastman et al. | |
| 6,694,800 B2 | 2/2004 | Weckstrom et al. | |
| 6,756,016 B2 * | 6/2004 | Miller et al. | 422/98 |
| 6,883,371 B2 | 4/2005 | Sugaya et al. | |
| 6,895,805 B2 | 5/2005 | Hoagland | |
| 6,923,054 B2 | 8/2005 | Liu et al. | |
| 7,080,545 B2 | 7/2006 | Dimeo, Jr. et al. | |
| 7,228,724 B2 | 6/2007 | Chen et al. | |
| 7,296,458 B2 | 11/2007 | Dimeo, Jr. et al. | |
| 7,296,460 B2 | 11/2007 | Dimeo, Jr. et al. | |
| 7,430,897 B2 | 10/2008 | Hu et al. | |
| 7,475,588 B2 | 1/2009 | Dimeo, Jr. et al. | |
| 2001/0009652 A1 | 7/2001 | Arno | |
| 2002/0029613 A1 | 3/2002 | Stetter et al. | |
| 2002/0051132 A1 | 5/2002 | Ohno et al. | |
| 2002/0198682 A1 * | 12/2002 | Huang et al. | 702/184 |
| 2004/0058488 A1 | 3/2004 | Arno | |
| 2004/0074285 A1 | 4/2004 | Dimeo, Jr. et al. | |
| 2004/0093853 A1 | 5/2004 | Hemingway et al. | |
| 2004/0163444 A1 | 8/2004 | Dimeo, Jr. et al. | |
| 2004/0163445 A1 | 8/2004 | Dimeo, Jr. et al. | |
| 2005/0103097 A1 | 5/2005 | Faltum et al. | |
| 2005/0193800 A1 | 9/2005 | DeBoer et al. | |
| 2005/0199496 A1 | 9/2005 | Dimeo, Jr. et al. | |
| 2005/0205424 A1 | 9/2005 | Dimeo, Jr. et al. | |
| 2005/0230258 A1 | 10/2005 | Dimeo, Jr. et al. | |
| 2006/0211253 A1 | 9/2006 | Chen et al. | |
| 2008/0134757 A1 | 6/2008 | Chen et al. | |

FOREIGN PATENT DOCUMENTS

| | | | |
|---|---|---|---|
| JP | 01-094255 A1 | | 4/1989 |
| JP | 5-166691 A | * | 7/1993 |
| JP | 5-267181 A | * | 10/1993 |
| JP | 09-105732 A | | 4/1997 |
| JP | 10-123084 A | | 5/1998 |
| JP | 2955583 B2 | | 10/1999 |
| JP | 2000-111507 A1 | | 4/2000 |
| JP | 2003-043001 A | | 2/2003 |
| SU | 857824 B | * | 8/1981 |
| SU | 1379632A A1 | | 3/1988 |
| WO | 93/08465 A1 | | 4/1993 |
| WO | 03062758 A1 | | 7/2003 |

OTHER PUBLICATIONS

"Micro-BetaCHIP Sensor (MCD)", 2005, Publisher: BetaTHERM Sensors Temperature Solutions, accessed at ww.betatherm.com.

Kurosawa, Shigeru, "Plasma polymerisation of fluorine contained polycyclic compounds: its application in chemical sensors", "Flourine in Coatings II, Paper 33", 2007, pp. 1-8.

Moritz, Werner, et al., "Monitoring of HF and F2 using a field-effect sensor", "Sensors and Actuators B", 1995, pp. 195-196, vol. 24-25.

Moritz, Werner, et al., "Chapter 10: Silicon-based sensor for fluorine gas", 1998, pp. 119-129, Publisher: American Chemical Society.

Peters, Laura, "Residual gas analysis: a technology at a crossroads", "Semiconductor International", Oct. 1997, pp. 94-101.

Quirk, Michael, et al., "Semiconductor Manufacturing Technology", "Semiconductor Manufacturing Technology", 2001, pp. 436 and 464, Publisher: Prentice Hall, Published in: Upper Saddle, NJ.

Van Zant, Peter, "Chapter 8: The ten-step patterning process—Surface preparation to exposure", "Microchip Fabrication: A Practical Guide to Semiconductor Processing, 5th Ed.", 2004, pp. 197-203, Publisher: McGraw-Hill, Published in: New York, NY.

Moritz, Werner, et al., "Gas sensors for fluorine using different semiconductor substrates", "The 11th European Conference on Solid State Transducers", Sep. 21, 1997, pp. 111-114.

Sanchez, J., et al., "Tin dioxide-based gas sensors for detection of hydrogen fluoride in air", "Thin Solids Films", 2003, pp. 132-136, vol. 436, No. 1 (Abstract only).

Golan, G., et al., "Active Thermoelectric Probing", "J. Optoelectron. Adv. Mat.", Aug. 28, 2003, pp. 1417-1422, vol. 5, No. 5.

Perry, Robert H., Ed., "Table 23-4. General Corrosion Properties of Some Metals and Alloys", "Chemical Engineer's Handbook, 5th Ed.", 1973, p. 23-36, Published in: New York, NY.

Stamate, E., et al., "Principle and application of a thermal probe to reactive plasmas", "Appl. Phys. Lett.", Apr. 29, 2002, pp. 3066-3068, vol. 80, No. 17.

Soboyejo, W.O., et al., EDS "Excerpt from: Advanced structural materials: properties, design optimization, and applications", 2006, p. 263.

Van Zant, Peter, "Microchip Fabrication, 5th Ed.", 1984, p. 198, Publisher: The McGraw-Hill Companies, Inc., Published in: New York, New York.

\* cited by examiner

RACE TRACK WEAVE

"S" WEAVE

"FIGURE 8" WEAVE

APPARATUS AND PROCESS FOR SENSING FLUORO SPECIES IN SEMICONDUCTOR PROCESSING SYSTEMS

CROSS-REFERENCE TO RELATED APPLICATIONS

This application is a continuation of U.S. patent application Ser. No. 11/057,735 filed on Feb. 14, 2005, and subsequently published on Oct. 20, 2005 as U.S. Publication No. 2005-0230258A1, which is a divisional of U.S. patent application Ser. No. 10/273,036 filed on Oct. 17, 2002 and subsequently issued as U.S. Pat. No. 7,080,545 on Jul. 25, 2006. The disclosures of all of the foregoing applications and patents are hereby incorporated by reference herein in their respective entireties, for all purposes, and the priority of all such applications is hereby claimed under the provisions of 35 U.S.C. §120.

GOVERNMENT RIGHTS IN INVENTION

Work related to the invention hereof was conducted in the performance of NIST ATP Program, Contract Number 70NANB9H3018. The Government has certain rights in the invention.

BACKGROUND OF THE INVENTION

1. Field of the Invention

The present invention relates generally to a sensor for fluoro species and to a method of sensing such species, having utility for monitoring of fluorine-containing compounds and ionic species in semiconductor process operations.

2. Description of the Related Art

In the manufacture of semiconductor devices, the deposition of silicon (Si) and silicon dioxide ($SiO_2$), and subsequent etching, are vital operational steps that currently comprise 8-10 steps or roughly 25% of the total manufacturing process. Each deposition tool and etch tool must undergo a periodic cleaning procedure, sometimes as often as every run, in order to ensure uniform and consistent film properties.

Currently, in etching operations, etch endpoints are reached when a prescribed amount of time has elapsed. Over etch, in which the process gas continues to flow into the reactor chamber after the cleaning etch is finished, is common and leads to longer process cycles, reduced tool lifetimes, and unnecessary global-warming-gas losses to the atmosphere (Anderson, B.; Behnke, J.; Berman, M.; Kobeissi, H.; Huling, B.; Langan, J.; Lynn, S-Y., *Semiconductor International*, October (1993)).

Similar issues are present in the etching of silicon nitride materials when SiN is utilized in semiconductor device structures.

Various analytical techniques, such as FTIR, Optical Emission Spectroscopy, and Ionized Mass Spectroscopy, can be used to monitor the etch process. However, these techniques tend to be expensive, and often require a dedicated operator due to their complexity.

It would therefore be a significant advance in the art to provide a reliable, low-cost gas sensing capability that will serve to improve the throughput and chemical efficiency of the equipment used for the deposition and etching of silicon-containing materials, including silicon, silicon nitride and silicon dioxide, by reducing and optimizing clean and etch times, and hence reducing chemical usage, lengthening equipment operating life, and decreasing equipment down time.

In addressing this need, micromachined gas sensor devices would conceptually be useful to provide high performance sensing, due to their amenability to fabrication of suspended structures that can be manipulated thermally in a rapid manner. Surface micromachined devices have been developed using standard 2-level CMOS processing. In the fabrication of process sensors for aggressive environments, however, a major problem is protection of the sensor platform, particularly micromachined elements where $SiO_2$ and/or $Si_3N_4$ membranes are employed, since these materials are rapidly etched in the process environment to which they are exposed to effect the sensing of the target gas component.

It would therefore be a significant advance in the art to provide a micromachined sensing device that is resistant to attack by the gas environment being monitored, e.g., where the gas environment to be monitored contains fluoro species or other corrosive agents or etchants.

SUMMARY OF THE INVENTION

The present invention relates generally to apparatus and method for sensing fluoro species in an environment susceptible to the presence of such species, such as an ambient environment, a gaseous effluent stream from a semiconductor manufacturing process, etc.

In one aspect, the invention relates to a gas sensor assembly comprising a free-standing gas sensing element coupled on a substrate to means for monitoring a change in at least one property of the gas sensing element upon contact thereof with a target gas species and responsively generating a control signal, wherein the gas sensing element is formed of a material exhibiting said change in contact with the target gas species.

A further aspect of the invention relates to a solid state sensor coupled in sensing relationship to a process chamber and arranged to withstand a corrosive condition within such process chamber.

Another aspect of the invention relates to a gas sensor assembly arranged to monitor a effluent from a semiconductor manufacturing plant or a fluid derived from the effluent, wherein the effluent or fluid derived therefrom is susceptible of comprising a target gas species, and the gas sensor assembly comprises a free-standing gas sensing element coupled on a substrate to means for monitoring a change in at least one property of the gas sensing element upon contact thereof with the target gas species in the effluent or a fluid derived from the effluent, and responsively generating a control signal, wherein the gas sensing element is formed of a material exhibiting such change in contact with the target gas species.

A still further aspect of the invention relates to a method of monitoring a fluid locus for the presence of a target gas species therein, said method comprising:

exposing fluid at said fluid locus to a free-standing gas sensing element formed of a material exhibiting a change in at least one property of the gas sensing element upon contact thereof with the target gas species;

monitoring said at least one property of the gas sensing element during step (a); and responsively generating an output signal when the gas sensing element exhibits said change in at least one property of the gas sensing element, indicating the presence of the target gas species in the fluid locus, or a change in concentration of the target gas species in the fluid locus.

In another aspect, the invention relates to a method of manufacturing a gas sensor assembly, comprising the steps of:

providing a base assembly including a substrate member having spaced-apart upstanding contacts thereon;

depositing a layer of support material on the base assembly between the contacts;

depositing on the layer of support material a layer of a sensor material; and removing support material under the layer of sensor material, to form a free-standing sensor material structure.

A further aspect of the invention relates to a method of manufacturing a gas sensor assembly, comprising the steps of:

providing a substrate member;

forming a trench in the substrate member;

depositing a support material in the trench;

depositing a layer of a sensor material over the trench and adjacent surface regions of the substrate member; and removing support material from the trench under the layer of sensor material, to form a free-standing sensor material structure overlying the trench.

Another aspect of the invention relates to a gas sensor assembly comprising a free-standing gas sensing element coupled on a substrate to means for monitoring a change in at least one property of the gas sensing element upon contact thereof with a fluoro species and responsively generating an output signal, wherein the gas sensing element is formed of a material exhibiting such change in contact with the fluoro species.

A further aspect of the invention relates to a solid state sensor coupled in gas sensing relationship to a process chamber and arranged to withstand a corrosive condition within such process chamber, wherein the solid state sensor comprises a free-standing gas sensing element arranged for contacting the corrosive environment and responsive to the contacting by change of at least one monitorable property of the gas sensing element, and a signal generator arranged to output a signal indicative of the change in such at least one property of the gas sensing element.

An additional aspect of the invention relates to a gas sensor assembly, comprising a substrate having deposited thereon a barrier layer for protection of the substrate from attack during gas sensing, a layer deposited on the barrier layer of a sensing material producing, in exposure to gas to be sensed in the gas sensing, a change in at least one property or response characteristic of the sensing material layer, and a cavity formed in the substrate member on a back side thereof, such cavity terminating at a back face of the sensing layer.

In a further aspect, the invention relates to a method of making a gas sensing assembly, comprising:

providing a substrate member;

depositing a barrier layer on the substrate member;

depositing a sensing layer on the barrier layer; and micromachining a backside cavity in the substrate member terminating at an interior face of the barrier layer.

Yet another aspect of the invention relates to a gas sensor assembly including a free-standing metal sensor element arranged for selective resistance heating of the element and exhibiting a change in at least one property of the element in contact with a fluoro species in a gaseous environment, and a signal generator operatively coupled with the sensing element to output a signal indicative of presence of a fluoro species in gas being monitored when the gas being monitored is contacted with the sensing element and the gas being monitored contains such fluoro species.

A still further aspect of the invention relates to a gas sensor assembly including an array of posts, and one or more free-standing metal sensor wire(s) woven about such posts to provide a woven wire structure for contacting with gas susceptible to presence of one or more target species therein with which the wire is interactive to produce a response indicative of the presence of the one or more target species.

In another aspect, the invention relates to a gas sensor assembly comprising a micro-hotplate structure including a free-standing gas sensing element responsive to presence of fluoro species by response indicative of presence or increase in concentration of such fluoro species. A further aspect of the invention relates to a gas sensor device for detecting fluoro species in a gas environment, comprising a fluoro species-resistant polyimide support structure and sensing wire supported thereon for contacting the gas environment, wherein the sensing wire responsively exhibits a monitorable change in exposure to the fluoro species.

A still further aspect of the invention relates to a gas sensing assembly comprising a free-standing gas sensing element responsive to exposure to fluoro species by a response indicative of said fluoro species, wherein said free-standing gas sensing element comprises a composite filament including a filament core having a fluoro species-sensitive material coated thereon, wherein said core material has a higher resistivity than said fluoro species-responsive material.

Yet another aspect of the invention relates to a gas sensor assembly comprising a free-standing gas sensing element coupled to connector pins of a microelectronic device package, wherein the free-standing gas sensing element is arranged for contact with a gaseous environment susceptible to the presence or change of concentration of one or more target gas species therein, and the free-standing gas sensing element is formed of a material that in exposure to the target gas species exhibits a response transmissible through the connector pins of the microelectronic device package.

Another aspect of the invention relates to a gas sensor assembly comprising a free-standing member on a substrate, wherein the free-standing member comprises a gas sensing element arranged for contact with a gaseous environment susceptible to the presence or change of concentration of one or more target gas species therein, and the gas sensing element is formed of a material that in exposure to the target gas species exhibits a response indicative of the presence or change of concentration of the one or more target gas species in the gaseous environment, with the free-standing member comprising a barrier layer of a material resistant to the target gas species, supporting the gas sensing element.

In a still further aspect, the invention relates to a gas sensor assembly comprising a free-standing gas sensing wire element woven onto or into an insulative scaffolding member and comprising a multiplicity of windings thereon to form a woven wire structure, wherein the wire element is formed of a material exhibiting a response in exposure to target gas species, and such wire element is coupled to circuitry to produce an output indicative of presence or change of concentration of target gas species in a gaseous environment when the wire element is exposed to the target gas species.

As used herein, the term "fluoro species" is intended to be broadly construed to encompass all fluorine-containing materials, including without limitation, gaseous fluorine compounds, fluorine per se in atomic and diatomic ($F_2$) forms, fluorine ions, and fluorine-containing ionic species. The fluoro species may for example include species such as $NF_3$, $SiF_4$, $C_2F_6$, $HF$, $F_2$, $COF_2$, $ClF_3$, $IF_3$, etc., and activated fluorine-containing species (denoted collectively as F*) thereof, including ionized fragments, plasma forms, etc.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
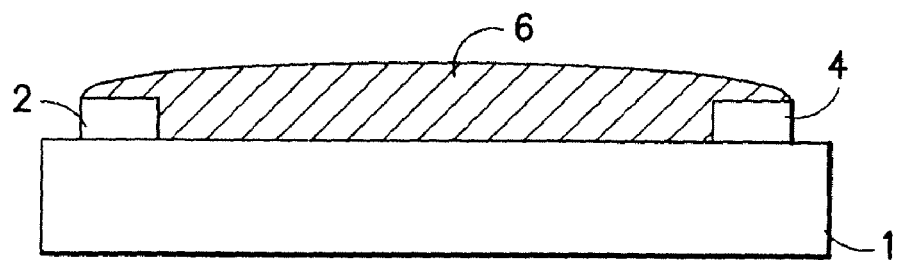
FIGS. 1, 2 and 3 are schematic illustrations depicting the process flow in the manufacture of a sensor according to one embodiment of the present invention.

While the invention is described more fully hereinafter with specific reference to applications in semiconductor process control, it is to be appreciated that the utility of the invention is not thus limited, but rather extends to a wide variety of other uses and applications, including, without limitation, deployment in life safety systems, room or ambient environment monitoring operations, and other industrial as well as consumer market gas sensing applications.

The present invention in one aspect thereof provides microelectromechanical system (MEMS)-based gas sensing capability for determining the endpoints of semiconductor chamber clean processes. MEMS-based sensing has not been commercially viable in such application, prior to the present invention, due to two major challenges, viz., (1) the development of thin film materials that will have a measurable response to the heavily fluorinated gases (typically, $NF_3$, $SiF_4$, $C_2F_6$, HF, and activated species thereof) that typically are employed in semiconductor chamber cleaning, and (2) the integration and packaging of such sensing films in a reliable form that will survive the harsh environments of such heavily fluorinated gases.

These have been formidable challenges, since current MEMS designs (for other, more benign gas environments) require deposition of the sensing metal layers on a silicon-based device structure, and subsequent bonding and packaging of the device into a chip carrier. This current fabrication approach entails a multi-step process, involving a corresponding multicomponent product sensor assembly in which each component is subject to chemical attack by the heavily fluorinated gases. While it may be possible to protect each of the respective components by developing a suitable encapsulation structure, such expedient adds further fabrication complexity, manufacturing time and cost to the product gas sensor device.

The present invention overcomes these obstacles in a manner enabling the use of a MEMS-based sensor device that is easily and inexpensively fabricated, and readily implemented for monitoring fluorinated gases in semiconductor chamber clean processes in an efficient, durable and reliable manner in the harsh chemical environment of such processes.

The fluorinated gas sensor device of the invention, as described more fully hereinafter, has two primary features that distinguish it as a breakthrough in the art. One such feature is the use in the device of free-standing metal elements, functioning as a sensing material and as optionally as a heat source (e.g., by resistive, conductive, or other heating thereof) for the gas sensing operation, as for example where it is desired to vary the sensing temperature from ambient conditions, or to match the temperature of a semiconductor chamber whose effluent includes the target gas species to be monitored. The second such feature relates to the packaging of the free-standing metal films, wherein the free-standing structure is able to be fabricated directly onto a standard chip carrier/device package so that the package becomes the platform of the device.

The invention thus provides a solid-state sensor that can be coupled in sensing relationship to a process chamber, e.g., a semiconductor process chamber, and can withstand a corrosive environment within the process chamber by appropriate selection of materials and sensing elements, as hereinafter more fully described.

The fluoro species sensor device of the invention may include a single sensing element in any of the numerous suitable forms described hereinafter.

Alternatively, the fluoro species sensor device may comprise a plurality of such sensing elements, wherein the multiple elements provide redundancy or back-up sensing capability, or in which different ones of the multiple sensing elements are arranged for sensing of different fluoro species in the stream or gas volume being monitored, or in which different ones of the sensing elements in the array are operated in different modes, or in interrelated modes, such as for production of respective signals that are algorithmically manipulated, e.g., subtractively, to generate a net indicating signal, or alternatively, additively to produce a composite indicating signal, or in any other suitable manner in which the multiplicity of sensor elements is efficaciously employed to monitor the flow of species in the stream or fluid volume of interest, for generation of correlative signal(s) for monitoring or control purposes.

As is well known, fluorine reacts with most metals, and gives rise to compounds that have a high, and sometimes, mixed oxidation state (Inorganic Solid Fluorides, Chemistry and Physics. Academic Press, 1985, Ed P. Hagenmuller). Many of the transition metals and noble metals (including, for example, but not limited to, Ti, V, Cr, Mn, Nb, Mo, Ru, Pd, Ag, Ir, Ni, Al, Cu and Pt) readily form various non-volatile fluorinated compounds in contact with fluorine gas components. The gas sensing device and method of the present invention use free-standing forms of these metals to detect the presence of fluorinated species in the gas being monitored.

Detection of the fluoro species of interest may be achieved in any suitable manner, e.g., by means of a change in resistance of the free-standing metal material as it reacts with fluorine-containing species.

It will be recognized that the choice of a specific material of fabrication for the free-standing fluoro species sensing element may vary in the preferred practice of the invention according to the character of the stream being monitored for the presence of fluoro species, and particularly according to the corrosivity of the target gas species being monitored or otherwise present in the monitored gas, and the corresponding corrosion-resistance of the sensing element material in such exposure.

For example, palladium in some aggressively corrosive environments may be less preferred in consequence of its etching by the monitored medium, than other sensing element materials of construction.

The choice of a specific sensing material of construction may be readily determined for a given end-use application of the invention, by simple experiment involving exposure of candidate gas sensing element materials of construction to the fluoro species-containing environment, and determining the suitability, e.g., corrosion-resistance or etch-resistance, of the candidate materials in such exposure.

The free-standing sensing element in fluorine detectors of the invention may be provided in any of numerous suitable forms, including, but not limited to, wires, filaments, foils, nanoporous free forms or coatings, electroplated metal, e.g., metal co-electroplated with liquid crystals, or thin films suspended above an air gap. These sensing elements may have tailored morphology, such as roughened surfaces, standard nanoporosity, or induced nanoporosity. In one embodiment of the invention, electroplated nickel is utilized as the fluoro species sensing material, and electroplated aluminum may also be employed to advantage, as well as electroplated forms of any other of the previously mentioned metals, as well as metals other than those specifically illustratively mentioned. The reaction of the fluorine compound with the free standing metal may be temperature-sensitive, and heating of the metal can be achieved by passing current through it. In this way, the gas sensing elements may be utilized in the gas sensing operation as self-heating structures, such character being enabled by the free-standing nature of the structure.

The resistance and behavior of the free-standing metal can be engineered by altering the geometry of the structure. For example, a free-standing wire can be thinned in any of a variety of ways, e.g., mechanically, chemically, electrochemically, optically or thermally, in order to increase the absolute resistance, as well as to increase the surface area-to-volume ratio of the metal, to thereby increase the sensitivity or improve the signal-to-noise ratio. Likewise, the geometry of a suspended thin film can be engineered by choosing the width, length and thickness of the film over the suspended area appropriately. Further, the material's physical properties can be engineered. For example, the composition can be modified either by alloying or doping, and the microstructure can be modified, e.g., by change in grain size, level of crystallinity, porosity (e.g., nanoporosity), surface area-to-volume ratio, etc.

It will therefore be apparent that the free-standing metal structure may be variously configured and modified as desired with respect to its form, conformation, physical properties, chemical properties and morphological character, within the skill of the art and without undue experimentation.

As discussed hereinabove, the free-standing metal structure of the sensor device of the invention can be readily fabricated directly onto a standard chip/carrier package, so that the package is effectively constituted as the platform for the device. This packaging is an important feature of the present invention in application to semiconductor process gas monitoring devices, since the heavily fluorinated environment characteristic of such semiconductor manufacturing application is an environment that is antithetical to the use of conventional MEMS-based gas sensor devices. The gas sensing device of the invention, by use of a free-standing metal structure as the sensing element that is integrated directly into a package, overcomes the susceptibility to chemical attack that has limited the ability of the prior art to use MEMS-based sensor devices in such applications.

The free-standing structure can be integrated as part of the device package in any suitable manner. For example, in the case of a free-standing wire sensing element, or a foil structure sensing element, the wire or foil structure can be spot welded directly to the packaging posts. The free-standing wire or foil can then be thinned-down in any suitable manner, e.g., mechanically, chemically, electromechanically, electrochemically, thermally, optically, etc. A preferred thinning technique involves laser micro-machining of the free-standing metal sensing element.

As another illustrative approach for integrating the free-standing metal sensing element into the device package, an insulation layer may be applied to the package for the device, followed by planarization of this insulator to expose the package pads, followed by thin film deposition to form the gas sensing element.

The thin film deposition may be carried out in any suitable manner, but preferably it is effected by physical vapor deposition, and most preferably it is achieved by sputtering or e-beam evaporation. A shadow mask may be employed to delineate the structure of the deposited film. The insulation layer material may be organic or inorganic, but is advantageously a material that can withstand the environment in which it used, i.e., it should be vacuum-compatible, etch-resistant, and non-contaminating. This integrated structure can be further modified as desired, e.g., by laser micro-machining. Laser micro-machining, for example, can be used to further thin the geometry as well as to etch away the insulating material, creating an air gap and thus yielding a free-standing thin film device structure.

The ability to integrate the free-standing structure into a standard microelectronic device package such as a chip carrier package, enables the gas sensor apparatus of the invention to be variously configured as a single-element device structure, or alternatively as a multi-element array, e.g., using varied metal structures, different geometries, or redundant structures operating at different temperatures, to enhance the gas detection capability of the overall sensing device. The number of pins (contact structures) in the device package is a limiting factor in determining the maximum size of the array, and the ready commercial availability of a wide range of multi-pin device package structures thereby correspondingly enables varying-sized arrays to be provided.

In instances where multiple metal sensing element structures are provided, different ones of the multiple metal structures may be constructed and arranged for sensing of different fluorinated species in the fluid environment being monitored, and/or same fluorinated species at different temperatures, and different geometries and configurations of sensing elements may be employed for redundancy and/or ensuring accuracy, etc. Alternatively, or additionally, different ones of the multiple sensing elements may be operated in different operating modes, e.g., resistively, conductively, pulsed, a DC mode, an AC mode, etc.

In connection with the use of arrays of gas sensing elements, advanced data processing techniques can be used to enhance the output of the sensor system. Examples of such techniques include, but are not limited to, the use of compensating signals, the use of time-varying signals, heater currents, lock-in amplifying techniques, signal averaging, signal time derivatives, and impedance spectroscopy techniques. In addition, advanced techniques that fall into the category of chemometrics may also be applied. These techniques include least squares fitting, inverse least squares, principal component regression, and partial least square data analysis methods.

The gas sensing element(s) of the sensor assembly of the invention may therefore be coupled in a suitable manner, within the skill of the art, to transducers, computational modules, or other signal processing units, to provide an output indicative of the present or change in amount of one or more fluoro species in the fluid environment being monitored.

Figure 2:
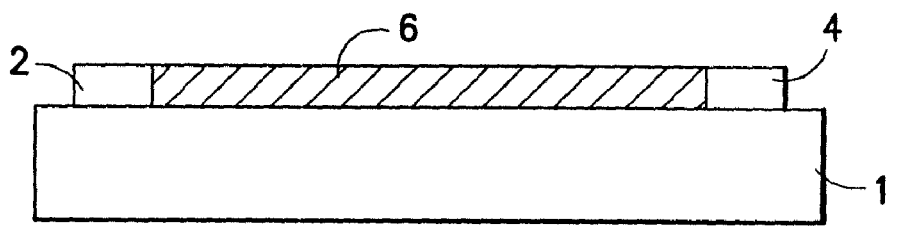
Figure 3:
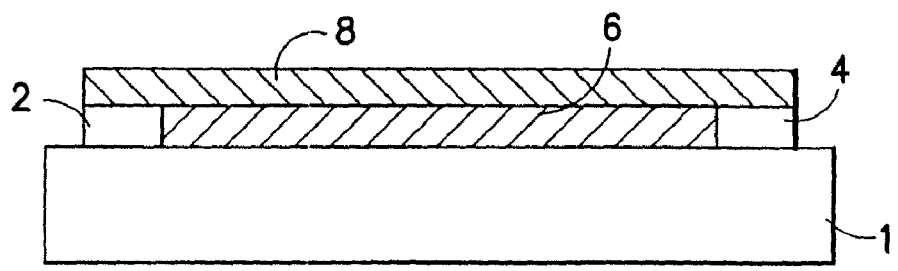

Referring now to the drawings, FIGS. 1, 2 and 3 are schematic illustrations depicting the process flow in the manufacture of a sensor according to one embodiment of the present invention, including the package fabrication of free-standing thin film elements to yield a gas sensor assembly.

As shown in FIG. 1, a base assembly, including substrate member 1 having contacts 2 and 4 thereon, which may for example comprise a TO-5 or TO-8 header, is first coated with plasma-resistant polymer 6, such as polyimide, or a commercially available SU-8 photoresist, between the contacts.

The excess material of the layer of polymer 6 then is polished off as shown in FIG. 2 by a suitable planarization step, to generate a flat surface for subsequent e-beam evaporation of sensing metal.

A thin film 8 of Pt or other suitable metal then is formed on the layer of polymer 6 by a suitable technique such as e-beam evaporation of the metal onto the contacts (and polymer), e.g., using a shadow mask (not shown in FIG. 3). Additional processing may include laser trimming to further modify the thin film shape, and to remove polyimide material in selected regions from under the thin film structure, e.g., with a laser ablation tool, to form a trench under the thin film gas sensor element.

The sensor assembly may thus comprise a thin film metal strip disposed over a surface of a sensor platform constituted by a VESPEL® polyimide flange or electrical feedthrough with a polyimide protective layer. In general, the sensor assembly may employ any number of flanges, e.g., KF flanges, and such flanges may be formed of a suitable material such as VESPEL® polyimide (commercially available from E.I. du Pont de Nemours and Company, Wilmington, Del.) or aluminum. In one embodiment, the sensor assembly fabrication includes press-fitting of TO heads into VESPEL® polyimide flange members. VESPEL® polyimide is a preferred polyimide material of construction in various embodiments of the invention as hereinafter more fully described, but it will be recognized that other polyimide or polymeric (e.g., polysulfone) materials of construction may alternatively be used.

Figure 4:
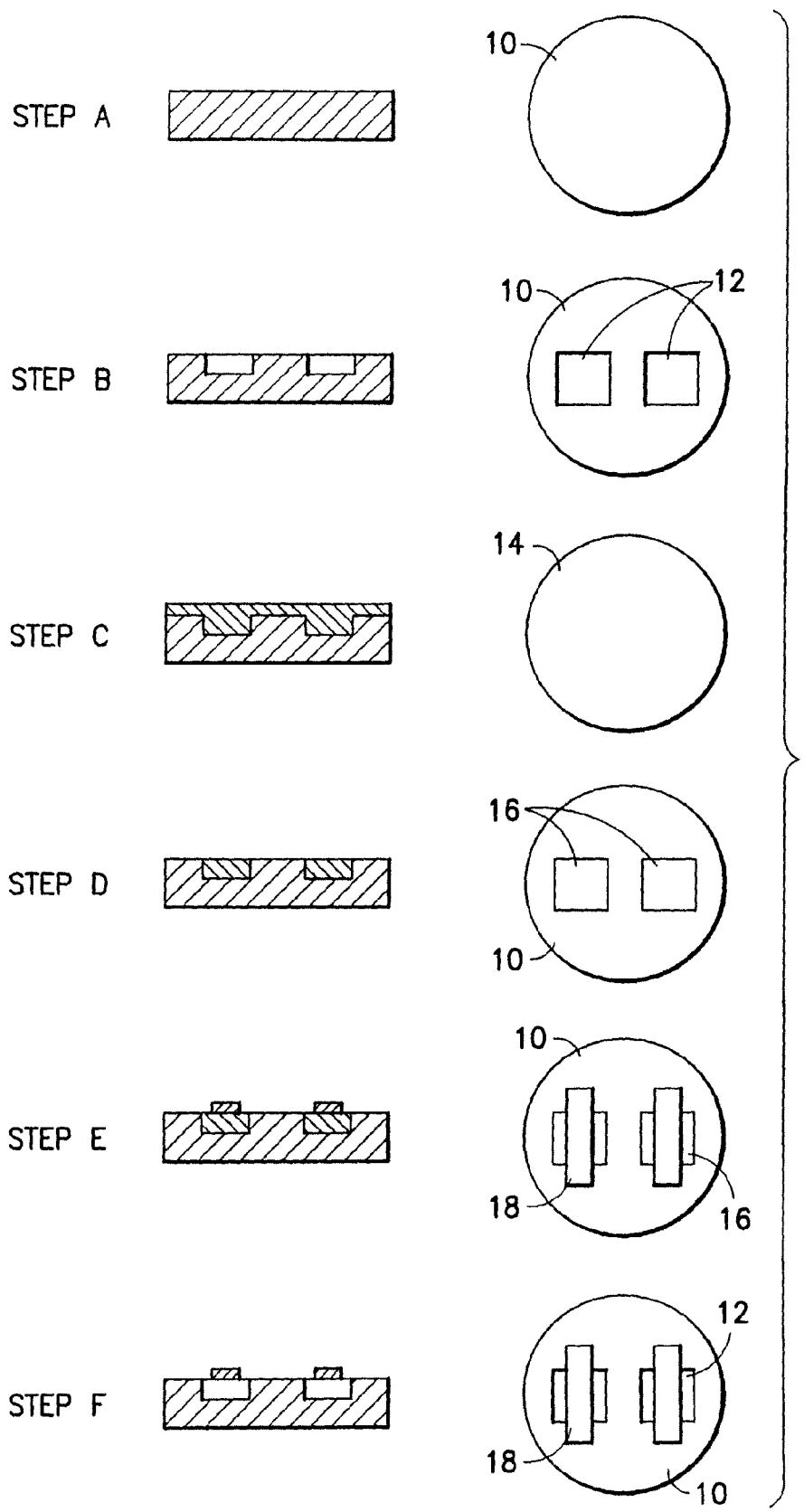
FIG. 4 depicts successive steps (Steps A through F) in the fabrication of a sensor assembly according to another embodiment of the invention.

In a preferred aspect of the present invention that avoids the problems of controlling the dimensions of the trench when laser ablation is employed to form a trench beneath the sensor metal film, and related issues of minimizing damage to the sensor element metal layer and avoiding redeposition of substrate material on the sensor element, the fabrication process methodology shown in FIG. 4 may be carried out to form a gas sensor assembly according to another embodiment of the invention.

FIG. 4 illustrates successive steps (Steps A through F) in the fabrication of the sensor assembly, in which each step is depicted with reference to a cross-sectional elevation view of the structure being fabricated on the left-hand side of the figure, and the arrow labeled with the step designation (see arrows A, B, C, D, E and F, in sequence, from the top to the bottom of the figure) connecting such cross-sectional elevation view with a corresponding top plan view of the structure, wherein the top plan view for each step is labeled with the reference numerals discussed in the ensuing description of the process.

In the FIG. 4 process, the substrate 10 is a VESPEL® polyimide flange (Step A).

Laser drilled trenches 12 are formed in the VESPEL® polyimide flange 10, producing the structure shown in Step B. While laser ablation is a preferred technique for such trench formation, other non-laser methods could be employed, e.g., selective chemical etching of the substrate, RIE techniques, etc.

A layer of sacrificial material 14 then is applied over the surface of the laser-drilled substrate (Step C) so that the trenches are filled with the sacrificial material. The sacrificial material preferably is a material that can be removed in subsequent processing by liquid- or gas-phase etching or other removal process. Examples include a polymeric material that is removable by ashing in the presence of $O_2$, or materials such as $SiO_2$ that are removable by a fluorine-containing plasma etch, or by appropriate chemical solution or solvent dissolution media.

Next (Step D), the surface of the structure is polished in a planarization operation, to remove the sacrificial material 14 from the surface of the flange surrounding the trenches, leaving trench deposits 16 of the sacrificial material. The planarization step improves the planarity of the substrate surface, and assists thereby in achieving good control of the geometry of the subsequently formed metal element. The planarization step is optional, and may be omitted in instances where good self-leveling behavior is achieved for the sacrificial material and it is possible to apply the sacrificial material into the trenches so as to be near-level with the adjacent surface of the substrate surrounding the trench cavity.

A sensing metallization material is then deposited (Step E) over the trench deposit 16 and top surface portions of the substrate adjacent the trench, to define the sensing element 18, as illustrated. The metal sensing element may be formed by deposition through a shadow mask, or alternatively as a blanket layer for subsequent patterning by photoresist and etching.

Finally (Step F), the sacrificial material is removed from the trenches 12, by etching or other suitable technique (solubilization, oxidative ashing, sublimation, etc.), so that the sensing element 18 overlies the trench 12 as an exposed thin film element that can then be coupled by leads to suitable electronics, e.g., an electronics control module including power supply and signal processing componentry (not shown in FIG. 4).

Such electronics are suitably arranged so that one or more properties of the sensing element 18 can be monitored. When the monitored property, e.g., electrical resistance or other suitable property of the metal sensor element, changes as a result of interaction with the fluoro species for which the metal sensor element is sensitive, the electronics provide a correlative output, e.g., a control signal, visual display output, etc., indicative of the presence or amount of the target gas species in the environment being monitored.

In an illustrative embodiment, the output may be a control signal that is employed to modulate a process from which the monitored gas is obtained. In a semiconductor manufacturing operation, such output may actuate a central processing unit (CPU), microprocessor, or other signal processing or signal-responsive means, to switch the process valves, and terminate a processing operation, or initiate a new process step or condition.

For example, on being contacted by fluorine compound(s) such as $SiF_4$, and/or other fluoro species, the voltage across the metal sensing element (as a component of an electrical circuit) may drop, indicative of an increase in resistance of the metal sensing element incident to its contact with a target fluoro species. Such voltage drop can be employed to generate a signal for process control purposes. The voltage drop can be employed to generate a signal that actuates an automatic control valve, to effect flow initiation, flow termination, or flow switching of a process stream in the semiconductor process system. The control signal alternatively may be employed to actuate a cycle timer, to initiate a new step in the process operation, or to signal that a maintenance event, such as change-out of a scrubber resin in an abatement process chamber, is necessary or desirable.

It will be appreciated that the change in properties of the metal sensing element can be exploited in any of a variety of ways, to effect the control of a process in relation to the sensing of the target gas (e.g., fluoro) species, within the skill of the art and without undue experimentation.

By way of further examples, the sensor assembly of the invention may be utilized in connection with a gas cabinet containing a supply of a fluoro species gas (such as a perfluoro species, e.g., a perfluorinated organometallic precursor for chemical vapor deposition operations), and the gas sensor assembly may be employed to determine the existence of a leak from the supply vessel or otherwise in the flow circuitry in the gas cabinet. The sensing of the fluoro species then may be utilized to actuate a source of bulk purge gas, to sweep out the interior volume of the gas cabinet and prevent the concentration of the fluoro species from reaching toxic or otherwise hazardous levels.

The sensor assembly may also be utilized in a monitoring unit for an ambient environment that is susceptible to the ingress or generation of fluoro species therein, or alternatively the sensor assembly could be a constituent part of a wearable gas monitoring unit that is arranged to actuate an alarm and/or a self-contained source of emergency breathing gas, for hazardous materials cleanup crews, firefighters in chemical complexes, workers in HF glass-etching operations, etc.

The metal that is employed in the metal sensor element of the present invention may comprise any suitable metal species that in exposure to the target gas species, e.g., one or more target fluoro species, produces a change that is monitorable and useful as an indicator of such target species (e.g., the presence of such target species, or changes in concentration of such target species).

Examples of metal sensor elements that may be employed for fluoro species sensing in the broad practice of the present invention, include, but are not limited to, one or more of Ti, V, Cr, Mn, Nb, Mo, Ru, Pd, Ag, Ir, Ni, Al, Cu and Pt. The metal may be in the form of an alloy or it may comprise a combination of metals, and composite sensing elements including a variety of metal species, or of metal and non-metal species in combination with one another, are contemplated within the broad scope of the present invention.

The metal sensor element in the sensor assembly of the invention is preferably of a high surface to volume (S/V) character, to facilitate rapid response, and to amplify the response relative to the substantially lower change in the gas-indicating bulk property that would otherwise occur in a low S/V conformation of the same sensor material.

Thus, preferred high responsivity forms of the sensor material include foils, films, filaments, needles, powders, etc., as well as metal-doped conductive threads, vapor-deposited metals on carbon nanotubes, and the like. The critical dimension of the metal sensing element—the thickness dimension for foils or films, or the diameter for forms such as filaments, needles, powders, etc.—desirably is less than 500 microns ($\mu m$), preferably less than 150 $\mu m$, more preferably less than 25 $\mu m$, still more preferably is less than 10 $\mu m$, and most preferably is in a range of from about 0.1 $\mu m$ to about 5 $\mu m$, as a balance of response speed and ease of fabrication considerations.

Foils and films, in addition to having a low thickness, e.g., in a range of from about 0.1 $\mu m$ to about 50 $\mu m$, desirably have small dimensional characteristics in the plane perpendicular to the thickness direction of the foil or film, again for reasons of responsivity. The lateral dimensions in such plane (x-y plane, where the z axis is the thickness direction) include a length (x-direction) and width (y-direction) that are advantageously less than about 10 cm, preferably being less than about 1 mm and more preferably less than about 100 μm, e.g., in a range of from about 20 μm to about 5 mm, as a balance of fabricational complexity and responsivity. The length of wires when used as a metal sensing element may be of any suitable length, particularly when used in woven structures as herein described. As a specific example, wires having a length of 7-15 cm and a diameter in a range of 75 to 150 μm are usefully employed in one embodiment of the invention. In general, suitable dimensions of sensor wires can be readily determined to provide correspondingly suitable signal-to-noise ratios for the intended applications.

In the context of the foregoing description, it is to be appreciated that the metal sensing element could be fabricated as a nano-scale element, albeit as a more costly gas sensor product than the typically millimeter/micrometer-scale elements discussed above.

The sensing element of the invention is a free-standing element, i.e., it has a sensing portion that is exposed to the fluid environment that is being monitored by the sensor for the presence of the target species, e.g., fluoro species, of interest, to maximize the sensitivity, response time and operating life of the sensing element.

In one embodiment, the free-standing gas sensing element may have a fibrous or filamentary conformation, in which the end portions of the elongate gas sensing element are bonded or otherwise coupled to contacts or other circuit components, and the intermediate portion of the element is unsupported and constitutes the free-standing section of the element, between its fixed ends. Correspondingly, the free-standing element may be fabricated in a foil or film conformation, in which portions of the foil or film are bonded or otherwise coupled to contacts or other circuit components, with the region of the foil or film intermediate the contacts or other circuit components being unsupported, and constituting the free-standing portion of the gas sensing element.

The packaging of the sensor device in a preferred aspect of the invention is facilitated by the formation of the sensor device directly on a standard chip carrier/device package, thereby simplifying the interconnections of the device to the associated microelectronic circuitry that enable the gas monitoring and control functions of the sensor device assembly. For example, electrical contact to the metal sensing element may be effected from the backside of the substrate by through-vias or pins disposed in appropriate locations to effect the necessary electrical interconnection.

As is apparent from the foregoing discussion, the gas sensor assembly of the invention is readily fabricated in a simple and reproducible manner, and enables sensing of fluoro species to be achieved in a cost-effective fashion, using conventional signal processing and control componentry to which the gas sensor assembly of the invention can be conveniently coupled.

The gas sensor assembly of the invention is readily applicable to monitoring of fluoro species in various industrial process operations generating such species, including semiconductor manufacturing operations such as chamber cleans, in which fluoro species are utilized for removing silicon oxides, silicon nitrides, and low dielectric constant (k<3.9) silicon-containing films such as carbon-doped silicon oxides, etc.

FIGS. 5-8 depict successive steps in the fabrication of a gas sensor assembly including a chemically resistant barrier layer as a membrane support material, in accordance with another embodiment of the present invention.

Figure 5:
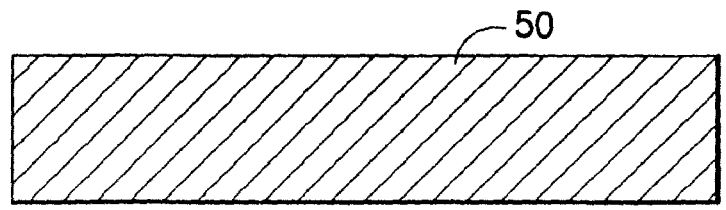
FIGS. 5-8 depict successive steps in the fabrication of a sensor assembly with a chemically resistant barrier layer as a membrane support material.
Figure 6:
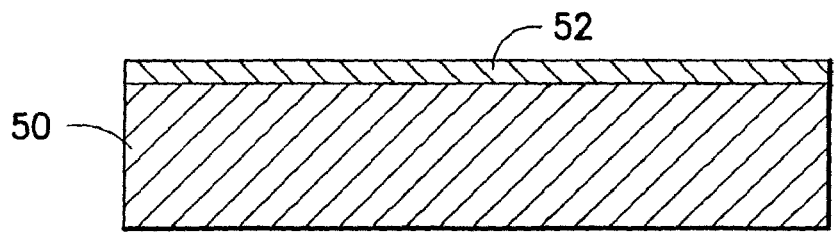

FIG. 5 shows a substrate member 50, formed of silicon or other suitable material. As illustrated in FIG. 6, the substrate member 50 is shown subsequent to deposition of a barrier layer 52 thereon. The barrier layer 52 protects the substrate 50 from attack by the gas to be monitored by the sensor, e.g., a gas containing one or more fluoro species, or other target component(s). The barrier layer may be formed of a suitable inorganic dielectric material, such as silicon carbide, diamond-like carbon, etc. Alternatively, the barrier layer may be formed of an organic material, e.g., a polyimide.

Figure 7:
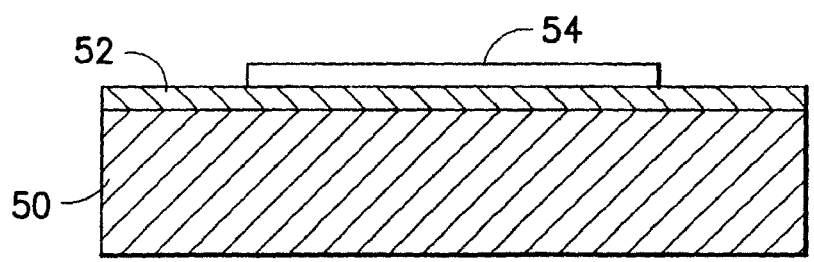

Subsequent to formation of the barrier layer by suitable deposition technique or other fabrication method, a gas sensing layer 54 is deposited, as shown in FIG. 7. The gas sensing layer may comprise a suitable metal, such as nickel, platinum, copper or aluminum, or other suitable material exhibiting a change of a material property, or otherwise exhibiting a suitable response, in exposure to the fluoro species or other target gas component to be sensed. The sensing layer 54 may be deposited in any suitable form and manner, such as in the form of a blanket layer for subsequent patterning by etching, or through a shadow mask.

A variety of designs is possible, and an array of devices of different dimensions may be advantageously employed to maximize the efficiency of the gas sensor assembly, in respect of generation and outputting of a plurality of signals for the monitoring of the one or more target gas species in the fluid environment being monitored by the assembly.

Figure 8:
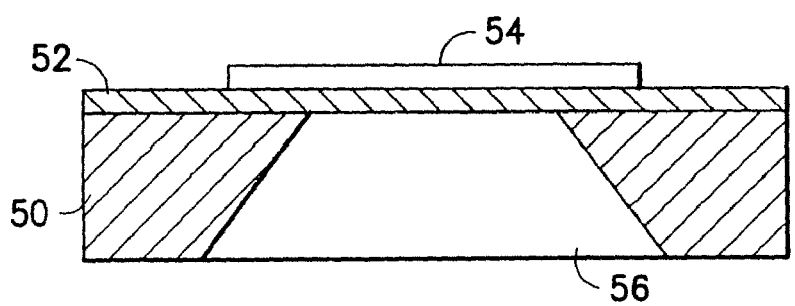

FIG. 8 depicts the sensor assembly after micromachining the backside of the substrate member 50 to form the cavity 56 on the back side of the assembly. Such cavity may be formed by standard etching techniques, or other material removal process.

The sensor assembly shown in FIG. 8 has the advantage that its fabrication avoids the provision of easily etched materials on the front sensing side of the assembly. The thickness and characteristics of the barrier layer 52 may be optimized by standard practices. Electrical contact to the metal sensor layer 54 may be effected by wire bonding at the top of the assembly, or through the barrier layer by buried contacts and through vias.

Although back-side etching is well-known for MEMS technology, the sensor assembly shown in FIG. 8 utilizes a chemically resistant barrier layer 52 as a membrane support material for the sensing layer 54, and thus fundamentally varies from prior known sensor structures employed in the art.

The sensing assembly shown in FIG. 8 after formation of electrical contacts may be inserted into a package from behind and sealed according to techniques known in the art. Alternatively, the sensor assembly after contact formation may be mounted on the front side of a robust flange material, e.g. a KF flange formed of VESPEL® polyimide or aluminum.

The present invention thus provides microelectromechanical (MEMS) gas sensor assemblies featuring free-standing metal sensor elements (i.e., metal sensor elements that are structurally unsupported over a portion, preferably at least a major portion, of their length or physical extent) that are integrateably directly into a device package. The resulting gas sensor assembly may be employed in a semiconductor manufacturing facility for determining the end point of semiconductor chamber clean processes (at the point of breakthrough of fluoro species or other target gas components in the effluent being monitored by the sensor assembly).

The fluoro species sensing elements used in gas detectors of the invention suitably comprise metals that readily form non-volatile fluorinated compounds when exposed to fluoro species in the gas environment contacted with the sensing element, resulting in a measurable change in electrical characteristics or other properties or response of the sensing element.

The free-standing architecture of the metal sensing element allows it to be used both as a sensing material and a heat source (e.g., susceptible to electrical resistance heating or other mode of heating), as well as maximizing the sensing area, as a result of the high surface-to-volume character of the sensing element, in the preferred forms previously described (foils, filaments, microparticulates, etc.). The integrated design of the sensing material and associated packaging obviates the problem of chemical attack by aggressive fluorinated gas species in the sensing environment, thereby achieving a fundamental advance in the art over standard silicon MEMS structures.

The gas sensor assemblies of the invention in a preferred mode of operation exhibit a measurable change in resistance of the free-standing metal sensing element as it reacts with fluorine-containing material in the sensed environment. The dimensions of the free-standing metal sensing element are selected so that the resistance (or other quantitatively measured response characteristic) is adequate for detection of the target gas species in the monitored environment, with acceptable sensitivity and signal-to-noise characteristics.

Such criteria have posed a substantial challenge to the prior art, but have been achieved in the gas sensor assembly of the present invention, by the provision of a free-standing metal sensor element having a three-dimensional architecture that produces a resistance or other response characteristic of the desired magnitude, with concomitant increased sensitivity and/or improved signal-to-noise ratio in relation to prior art gas sensor devices.

In a specific embodiment, the fluoro species (e.g., $NF_3$, $SiF_4$, $F_6$, HF, etc., and activated species thereof) gas sensing assembly of the invention utilizes free-standing metal structures, e.g., wires, as the sensing element and heat source for the sensing operation, wherein the metal structures are integrated with microelectronic device packaging, by spot-welding directly to the packaging posts of the microelectronic package, e.g., a standard chip carrier package.

In such embodiment, the posts advantageously are arranged in an array, preferably such that the heads of the posts are aligned in a same horizontal two-dimensional plane, with equal spacing between adjacent posts.

To ensure sufficient absolute resistance production by the gas sensor assembly, the length of the sensing element (wire) may be varied while keeping the wire diameter constant within manufacturing tolerances. When the wire length is substantially larger than the distance between posts, the wire has a susceptibility to coil uncontrollably between anchoring points on adjacent posts. Such susceptibility is overcome using a three-dimensional packaging architecture in accordance with a further aspect of the invention, such that wire lengths may be made considerably longer, to increase absolute device resistance and signal-to-noise ratios, while maintaining strict linear control of the wire position, as hereinafter described in greater detail. Various architectures may be utilized, in which metal packaging posts or machined VESPEL® polyimide is employed to control wire position in three dimensions.

In an illustrative packaging post architecture according to one embodiment of the invention, packaging posts formed of a suitable (electrically and thermally) insulating material are used as a three-dimensional framework around which sensor wires are woven. Wires in such architecture are electrically contacted at their terminii to separate posts, as for example, by spot-welding or by other suitable method of electrical contact such as press-fitting. Intermediate the anchored terminii of the wires, the wires are woven around the post. The extent of weaving and the number of posts incorporated in the architecture can be selectively varied to enable the desired length of the sensing wire to be achieved.

Regardless of the method of weaving of the wire, two principal criteria must be observed, viz., (i) that the wires not contact along their own length or with other wires, and (ii) that the wires not contact the metal of the posts except at the points of intended electrical contact. The second criterion necessitates that the posts be sheathed with an insulating material except at the points of intended electrical contact. Posts in the architecture that do not function as intended electrical contact points for any of the wires of the gas sensor assembly need not be metal, but can be formed of VESPEL® polyimide, or other suitable fluoro species-resistant insulating material.

Figure 9:
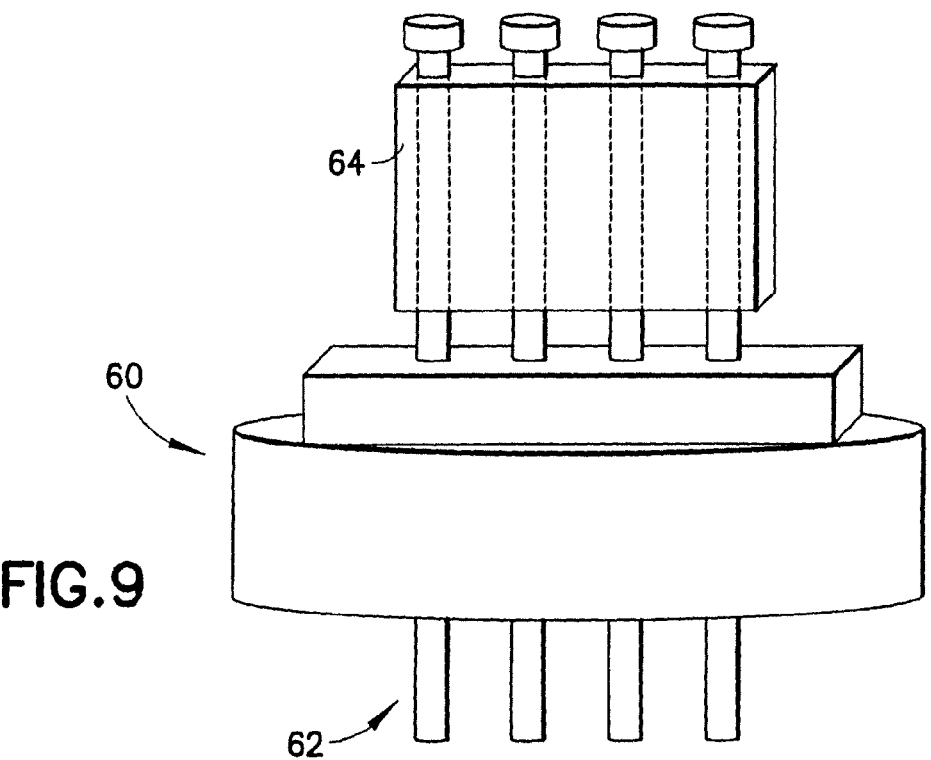
FIG. 9 is a schematic representation of a gas sensor assembly, including sensor wire woven in a vertically-oriented plane.
Figure 10:
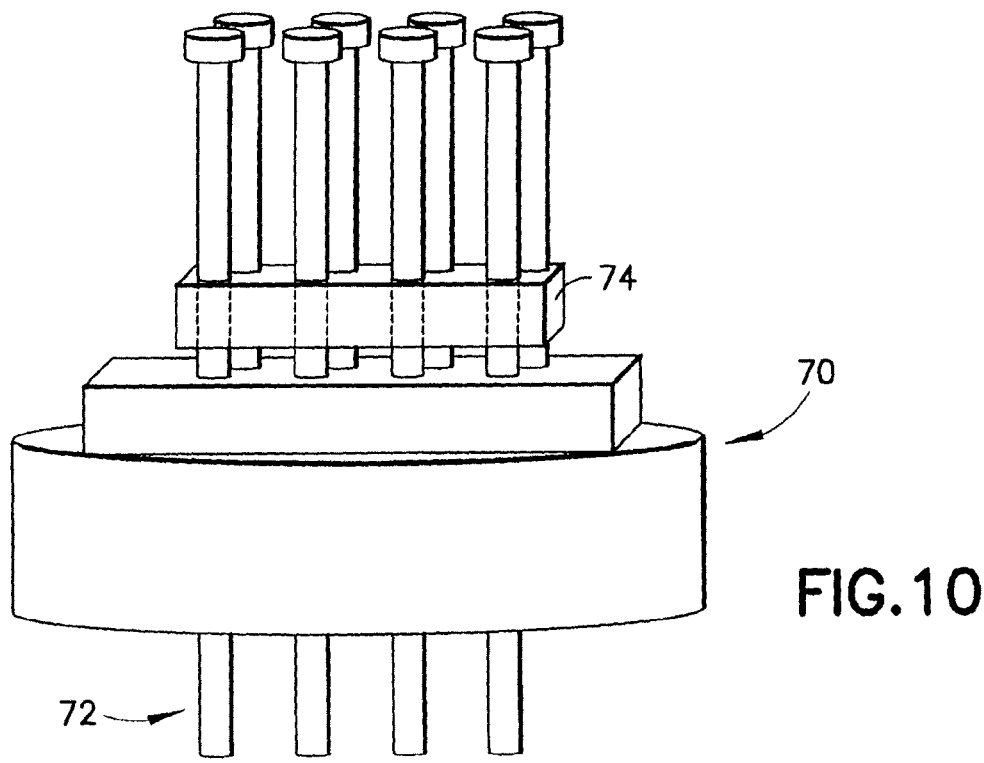
FIG. 10 is a schematic representation of a gas sensor assembly, including sensor wire woven in a horizontally-oriented plane.

A wide variety of techniques may be employed, consistent with the foregoing criteria, to achieve a desired wire length, and thus absolute resistance, in the packaging post architecture. Two general categories of such techniques may advantageously be employed—those in which the sensor wire is woven around the posts to form a woven structure in a vertically-oriented plane, as for example is shown in FIG. 9, in which the gas sensor assembly 60 comprises an array of posts 62 and the "vertical" weave 64 of sensor wire forms a woven structure in a vertically-oriented plane, and those techniques in which the sensor wire is woven around the post to form a woven structure in a horizontally-oriented plane, as for example is illustrated in FIG. 10, wherein the gas sensor assembly 70 comprises an array of posts 72 featuring a "horizontal" weave 74 of sensor wire.

The specific method of weaving of the sensor wire within a horizontal or vertical plane may be additionally varied in the practice of the invention.

Figure 11:
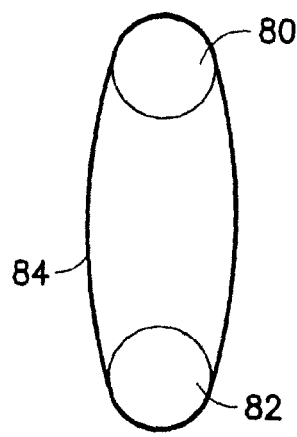
FIG. 11 is a schematic representation of a sensor wire wrapped around posts in a racetrack pattern.

For example, the sensor wire may be wrapped around the supporting posts in a racetrack pattern, as shown in FIG. 11, illustrating posts 80 and 82 and the racetrack winding 84 or sensor wire, but care must be taken to avoid forming a wire loop acting as a radio frequency inductor, since it thereby may be unsuitable for sensor usage due to spurious interference signals.

Figure 12:
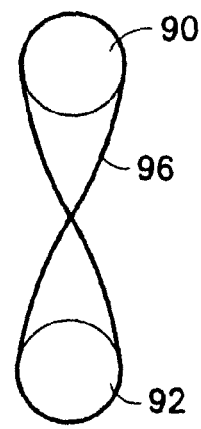
FIG. 12 shows a figure-eight pattern of sensor wire woven on support posts.
Figure 13:
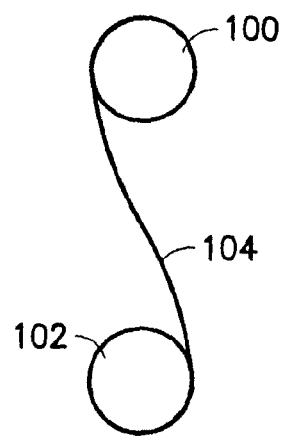
FIG. 13 shows an "S"-shaped conformation of sensor wire wrapped on supporting posts.

Other weaving patterns include the figure-eight pattern shown in FIG. 12, wherein the posts 90 and 92 support a figure-eight conformation of sensor wire 96, and the "S"-shaped weaving pattern shown in FIG. 13, wherein the posts 100 and 102 support the "S"-shaped conformation of sensor wire 104.

In addition to such weaving conformations, any number of weaving arrangements may be employed within the skill of the art. A matrix may be constructed for the purpose of representing possible permutations of weaving that can be applied to the sensing devices. For example, a vertical weave post assembly may be fabricated utilizing the "racetrack" weaving technique shown in FIG. 14, the "S"-shaped weaving technique shown in FIG. 15, or the figure-eight conformation shown in FIG. 16.

Figure 14:
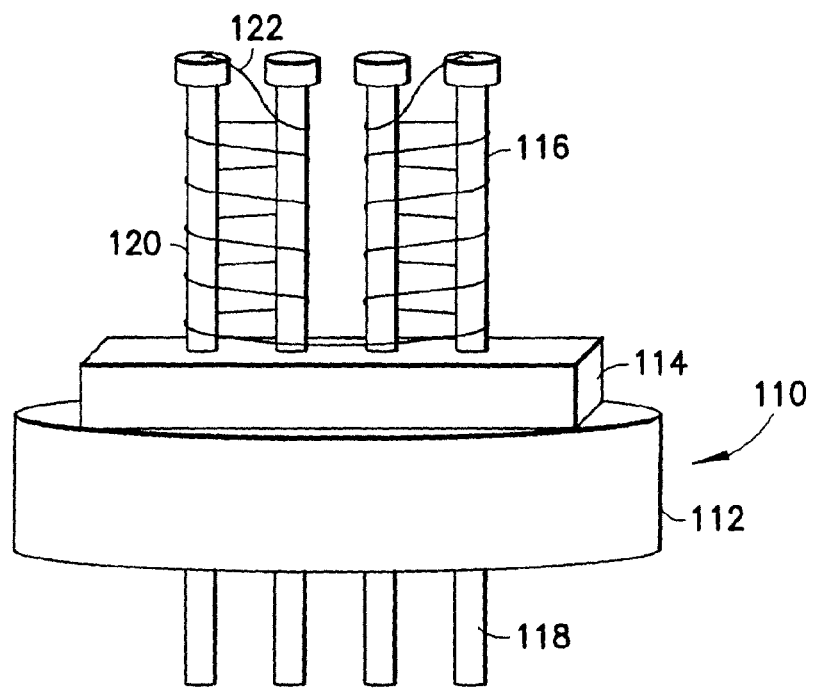
FIG. 14 shows a vertical weave gas sensor assembly utilizing a racetrack weaving technique.

FIG. 14 depicts a gas sensor array 110 including a flange 112 supporting a VESPEL® polyimide block 114, and an array of posts 116 fabricated of metal, as shown at the exposed post portions 118 below the flange, and the insulating material-sheathed portions 120 of the posts above the VESPEL® polyimide block 114, as illustrated. The sensor wire 122 is illustrated as having a racetrack conformation, of a type as shown for example in FIG. 11.

Figure 15:
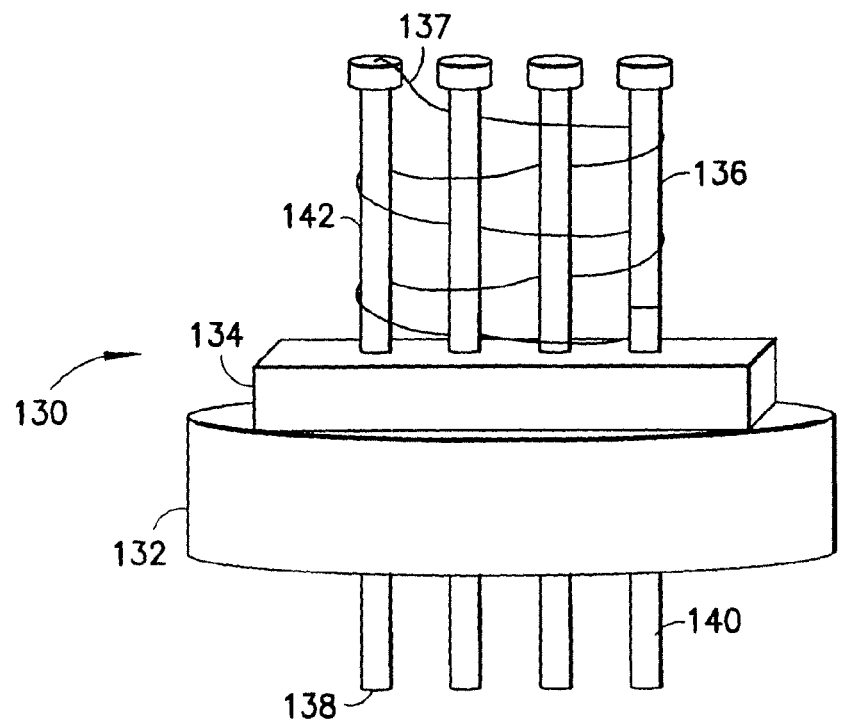
FIG. 15 shows a woven gas sensor assembly having an "S"-shaped weave.

FIG. 15 depicts a gas sensor assembly 130 including a flange 132 supporting a VESPEL® polyimide block 134 and an array 136 of posts 138, of which exposed metal portions 140 are shown below the flange and insulating material-sheathed portions 142 are shown above the VESPEL® polyimide block, wherein the gas sensor wire 137 is woven in an "S"-shaped conformation, of a type as shown in the plan view of FIG. 13.

Figure 16:
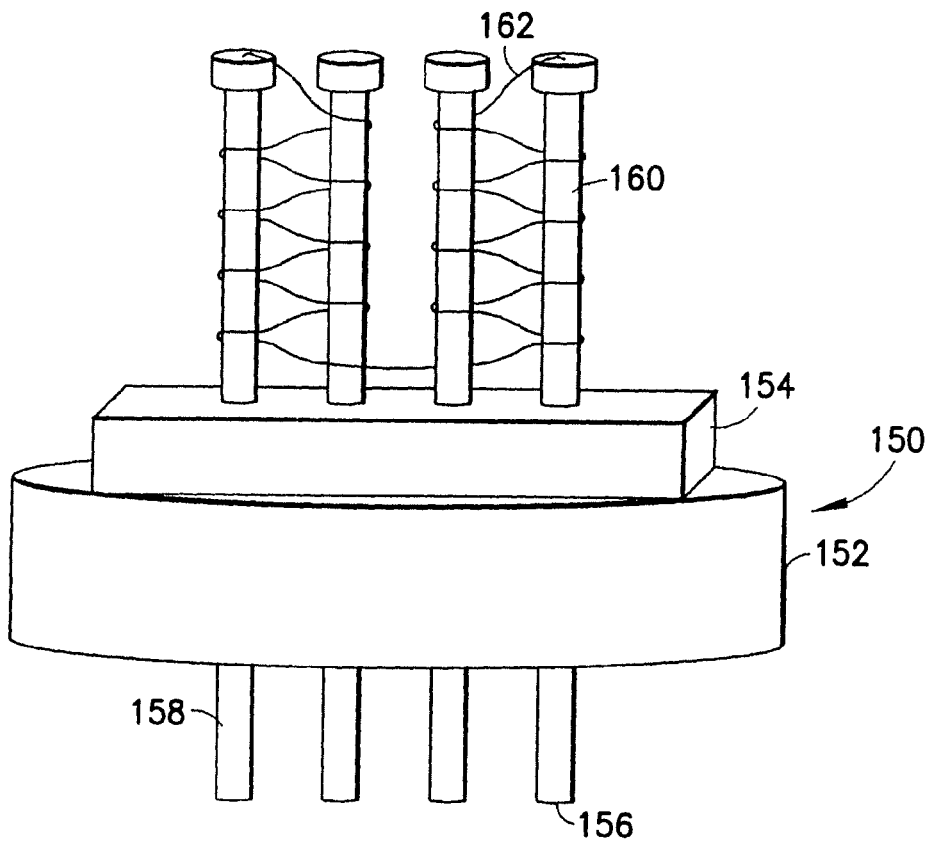
FIG. 16 shows a figure-eight conformation of weaving in a gas sensor according to another embodiment of the invention.

FIG. 16 depicts a gas sensor assembly 150 including a flange 152 and VESPEL® polyimide block 154 with an array of posts 156. The exposed metal portions 158 of the posts are shown below the flange 152 and the insulation-sheathed portions 160 of the posts are shown above the VESPEL® polyimide block 154. The wire weaving pattern of the sensor wire 162 in FIG. 16 is of a figure-eight conformation, of a type as illustrated in FIG. 12.

Figure 17:
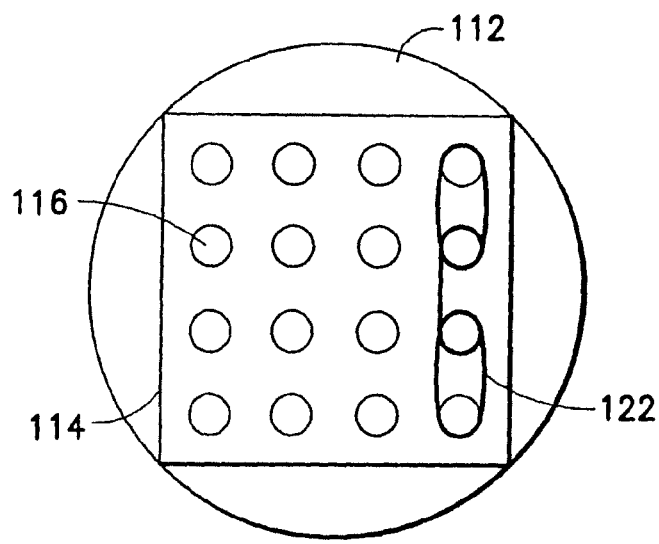
FIG. 17 is a top plan view of the gas sensor assembly of FIG. 14.
Figure 18:
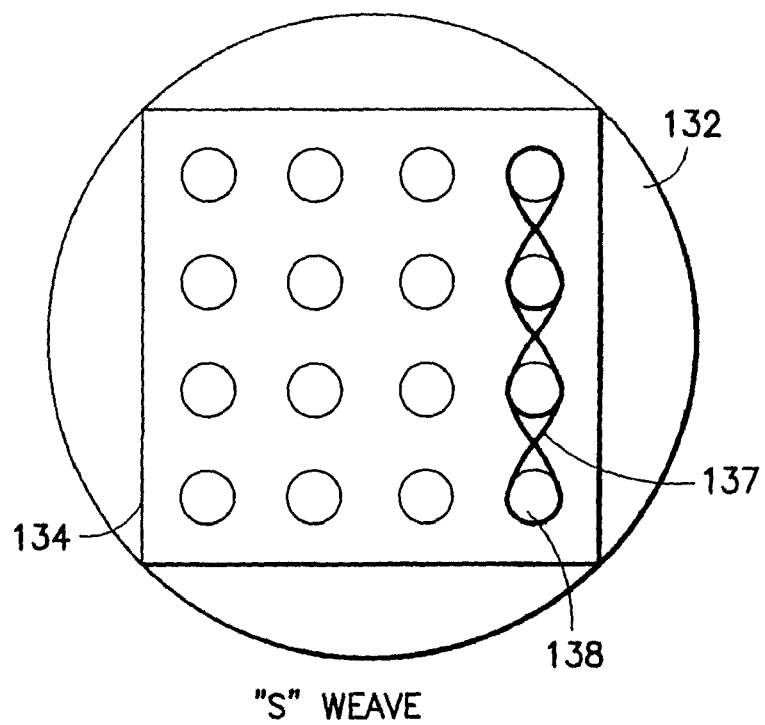
FIG. 18 is a top plan view of the gas sensor assembly of FIG. 15.
Figure 19:
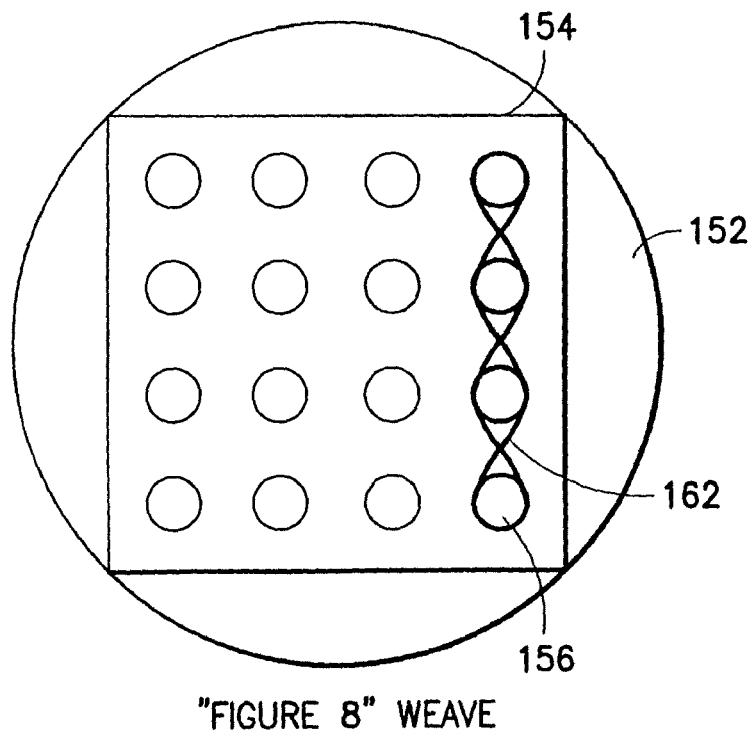
FIG. 19 is a top plan view of the gas sensor assembly of FIG. 16.

FIGS. 17, 18 and 19 show top plan views of the gas sensor assemblies of FIG. 14, FIG. 15 and FIG. 16, respectively.

The multi-post arrays of the gas sensor assemblies of FIGS. 17, 18 and 19 are readily adapted to test various sensing wire materials of construction, and in each of FIGS. 17-19, the far-right vertical row of posts is shown as having the specific conformation of wire previously described. It will be appreciated that successive vertical rows (progressively left of the row shown with the sensor wire on the posts) may comprise wires formed of different sensing metals, whereby a matrix of weaving techniques and different sensing metals is provided. Such a matrix permits testing of each of the permutations to determine a most effective packaging post/sensing wire weaving design in a given application of the present invention.

The gas sensor assembly of the invention in another aspect may utilize a machined VESPEL® polyimide architecture. VESPEL® polyimide is a polyimide having high dielectric strength, high heat resistance, high compressive strength and excellent dimensional stability, and such material has been determined by the present inventors to possess a very high resistance to attack by fluoro species. VESPEL® polyimide may therefore be used as a material of construction for a three-dimensional framework for weaving of sensing wires.

Other fluorine-resistant solid materials may also usefully be employed in the broad practice of the present invention, but VESPEL® polyimide has been found to be highly efficacious and is preferred in this aspect of the invention.

Utilizing a three-dimensional framework for weaving of sensing wires with a VESPEL® polyimide structure, electrical contact of the sensing wires is made as in the previously described embodiments to the metal packaging posts, however the metal posts may be relieved of their dual functionality requirements as electrical contacts and wire scaffolding elements by concurrent use of a scaffolding support structure for the gas sensing wires or other free-standing gas sensing elements.

In such arrangements where electrical contact posts are used in combination with scaffolding structures to support free-standing wires or other gas sensing elements, the metal posts do not require any insulation. Thus, intermediate anchored terminii, gas sensor wires may be woven around insulative material structures such as VESPEL® polyimide scaffolding members, and such scaffolding members may in turn be mounted on flanges or other substrate or support elements.

VESPEL® polyimide is commercially available in block and cylindrical forms as well as in powder form, which may be pressure molded to any desired shape. Subsequent machining of the block, cylinder or molded VESPEL® polyimide material, provides structure(s) suitable for scaffolding of the sensing wire in a three-dimensional architecture.

Controlled weaving of the sensing wire into or around such scaffolding using the previously discussed techniques for packaging post-based designs, allows the sensing wire to achieve necessary length characteristics, and corresponding absolute resistance required for effective fluoro species sensing. The VESPEL® polyimide material, or other fluorine-resistant solid material, may be machined in a fashion that allows it to manipulate the position of the wires, as shown in the following illustrative embodiments.

Block, cylinder or molded VESPEL® polyimide material may be machined in any of various ways to produce structures on or into which the sensing wire may be woven. For example, cuts may be made into the VESPEL® polyimide material to produce channels through which wires may be woven. Such cuts may penetrate completely through the material, or terminate at a prescribed depth, with the uncut material below the cut creating a "shelf" to control the vertical position of the wire. Additionally, vertical columns created on either side of a cut may act as "posts" around which the wires may be wound.

Figure 20:
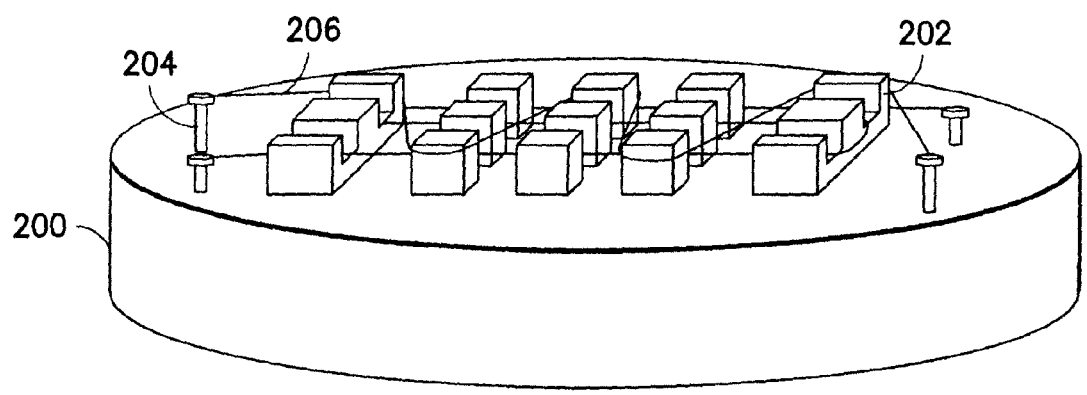
FIG. 20 illustrates a gas sensor assembly including a VESPEL® (a registered trademark of E.I. du Pont de Nemours & Co., Wilmington, Del.) polyimide block element machine with orthogonal cuts forming shelves for controlling the vertical position of sensing wire.
Figure 21:
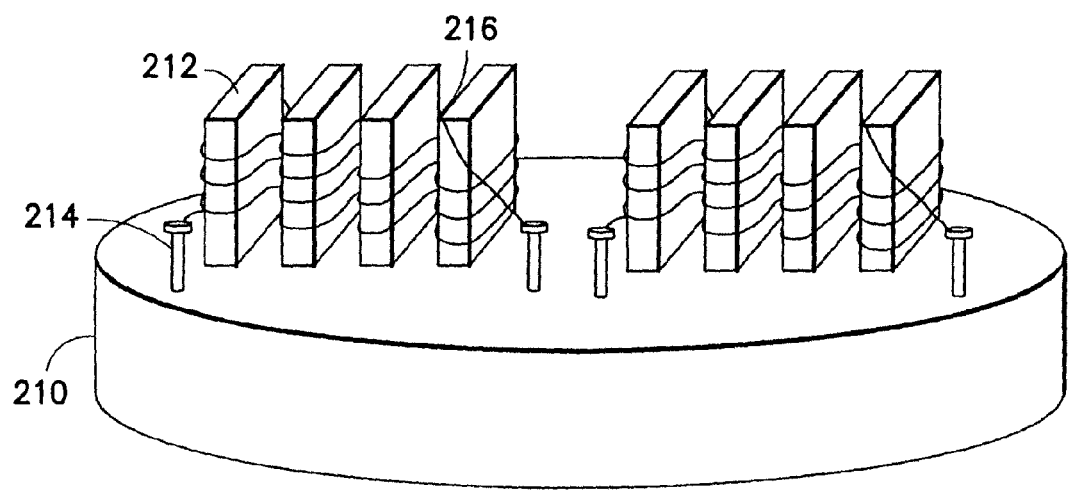
FIG. 21 depicts a gas sensing assembly including a flange and VESPEL® polyimide block element machined with complete parallel cuts to form posts about which sensor wires can be woven.

FIGS. 20 and 21 show respective VESPEL® polyimide structures utilizing orthogonal vertical cuts with "shelves" as illustrated in FIG. 20, and parallel vertical cuts through the VESPEL® polyimide block to create channels and posts, as shown in FIG. 21. Wires may be woven in these embodiments utilizing any of the various patterns previously described. The cut VESPEL® polyimide device designs are easily adapted to include arrays of different or multiple sensing wires. As with packaging post sensor designs, a matrix may be fabricated with all possible cut VESPEL® polyimide structures and all of the weaving patterns, such that sensors of all desired design permutations are presented for assessment, and empirically-based selection of the best design for a given gas sensing application.

FIG. 20 illustrates a gas sensor assembly comprising flange 200 on which is disposed VESPEL® polyimide block elements 202, which together with metal posts 204 provide support structure for weaving of sensor wires 206 as illustrated. The VESPEL® polyimide block elements are machined with orthogonal cuts with some incomplete cuts for the purpose of constructing shelves to control the vertical position of the sensing wire.

FIG. 21 depicts another gas sensing assembly including a flange 210 on which is disposed an array of VESPEL® polyimide block elements 212 and posts 214 for support of sensing wires 216. The structure shown in FIG. 21 features VESPEL® polyimide block elements that are machined with complete vertically-oriented parallel cuts, creating posts between the successive cuts, around which the wires can be woven. Both of the gas sensor assembly structures illustratively shown in FIGS. 20 and 21 utilize an "S"-shaped weaving pattern.

Gas sensor assemblies of the invention may also be fabricated in which VESPEL® polyimide elements have holes drilled therethrough to create a "pegboard" structure through which wires may be threaded to produce an architecture for support of lengthy sensing wires.

Such approach is illustrated by the exemplary gas sensing assemblies shown in FIGS. 22-25.

In additional to utilizing VESPEL® polyimide elements in the form of planar sheets of material with holes drilled therein, non-planar "pegboard"-type structures of other widely varied geometries may also be employed as scaffolding elements for sensing wires. For example, by drilling out the center of a VESPEL® polyimide cylinder, a tube may be produced. Further drilling of smaller holes along the sides of the tube creates a cylindrical "pegboard"-type framework through which sensing wires can be threaded and supported such that the position of the wire along its entire length can be controlled.

Many variations are possible for such "pegboard"-type scaffolding, which may be varied in respect of the numbers and dimensions/shapes of VESPEL® polyimide support elements, the numbers and drilling patterns of holes, and the arrangements of threading and weaving the wire through such holes. Arrays of sensing wires may easily be constructed using such "pegboard" architectures, and weaving styles and patterns may be selectively varied. Again, a matrix may be constructed of possible permutations of device designs, for purposes of assessing a best possible architecture for a given target gas species sensing application.

FIGS. 22-25 each include respective side, cross-section (except in the case of FIG. 22), and top views of respective examples of sensor devices utilizing machined VESPEL® polyimide structures as "pegboard"-type scaffolding for fabricating sensing wire arrays.

Figure 22:
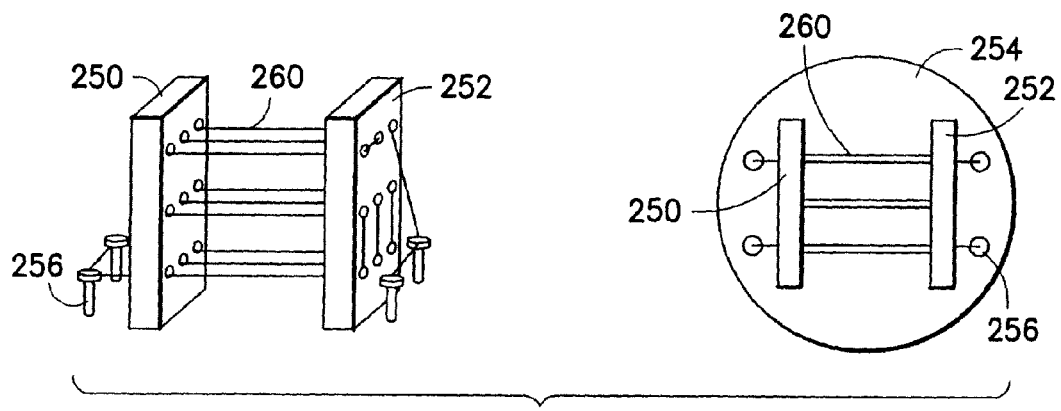
FIG. 22 illustrates a foraminous VESPEL® polyimide element array and sensing wire assembly.

FIG. 22 shows VESPEL® polyimide elements 250 and 252 disposed on a flange 254, along with metal contact posts 256. The VESPEL® polyimide elements 250 and 252 each contain a multiplicity of holes through which sensing wire 260 is threaded (there is only a side view and top view of the gas sensor assembly in FIG. 22. whereas respective side view, cross-sectional view and top view representations are shown in each of FIGS. 23-25). The arrangement shown in FIG. 22 provides a horizontally-woven array utilizing an "S"-shaped weaving pattern.

Figure 23:
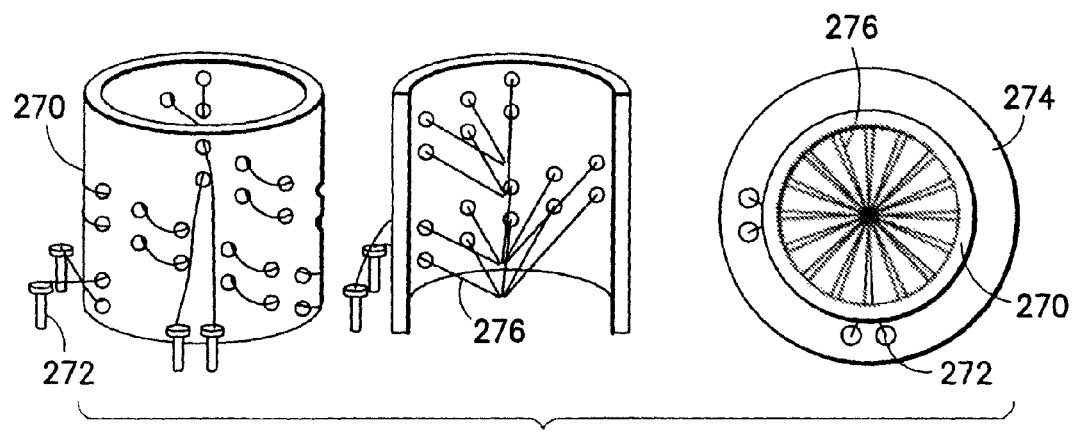
FIG. 23 shows a cylindrical VESPEL® polyimide element with sensor wire woven in a spiral array.

FIG. 23 shows a cylindrical VESPEL® polyimide element 270 in cooperation with metal posts 272 on a flange 274, in which sensing wire 276 is woven on the VESPEL® polyimide element in a spiral array.

Figure 24:
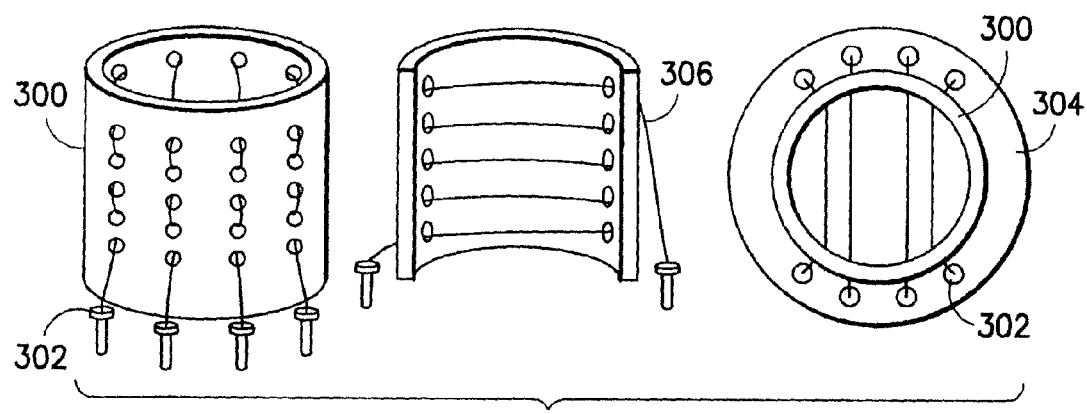
FIG. 24 illustrates a cylindrical VESPEL® polyimide element providing a support structure for vertically woven sensing wire.

FIG. 24 shows another cylindrical VESPEL® polyimide element 300 and metal posts 302 on a flange 304 providing a support structure for vertically woven sensing wire 306, as illustrated.

Figure 25:
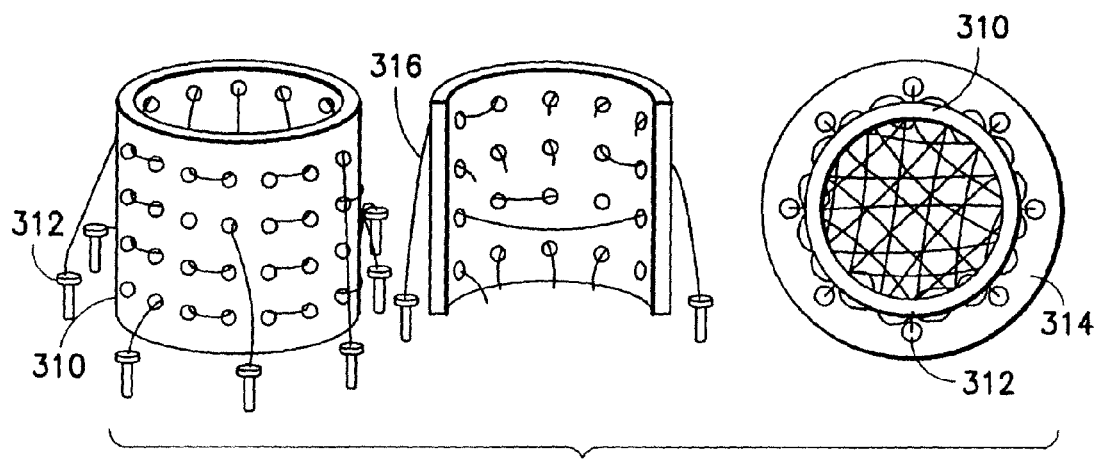
FIG. 25 shows a cylindrical VESPEL® polyimide element and an "S"-shaped weaving pattern of sensing wire.

FIG. 25 shows a cylindrical VESPEL® polyimide element 310 in combination with metal posts 312 on a flange 314 for provision of an "S"-weaving pattern of sensing wire in a horizontally woven arrangement.

In another aspect, the invention contemplates arrays of micromachined chemical sensor devices, wherein the micromachined chemical sensor devices have coatings comprising organic and/or inorganic sensor material that is reactive with the target species to be monitored. The sensor coatings in exposure to a gaseous environment containing the target gas species yield physical, electrical, and/or other changes that are indicative of the presence of the target species in the monitored environment. Such micromachined sensor arrays are usefully employed for sensing of fluoro species in the monitored environment.

In a particular aspect described more fully hereinafter, the gas sensing devices of the invention may include micro-hotplate sensing structures.

By using an array of sensors, multiple species of target components can be detected. For example, if an array of four sensing elements is employed, and each element has been designed to detect specific target species, four such species can be detected simultaneously. If, as is frequently the case, coatings that are specific to interaction with only one target species are difficult to produce, responses from multiple devices can be combined or otherwise algorithmically manipulated in reference to one another, to positively identify presence and concentration of target species.

For example, the responses from six non-specific sensors can be combined to produce an unambiguous identification of three target gas species. Additionally, sensors within a multi-element array can be individually operated at different conditions, e.g., different temperatures, further expanding the number of variables available to produce a unique sensing capability.

Further, by using an array of sensing elements, a number of redundant sensors can be incorporated in one package. The array can be brought into use sequentially as regards component sensor elements, thereby expanding the lifetime of the overall sensor assembly package, or permitting the use of sensor coatings that are consumed in the sensing process.

As an example, an array may utilize a polymer coating to suppress reactions with sensors that are not being used. At the time of use, the temperature of a particular array element may be selectively altered to melt or burn away the polymer coating and expose a reactive coating. Additional elements can be brought on-line in a similar fashion, as needed.

A number of advantages are inherent in the use of micro-machined sensor elements for fabricating a sensor array. These advantages include, without limitation, miniaturization of the sensor elements, ease of array fabrication, suitability for high-volume, low-cost manufacturing, low power consumption, and the ability to accommodate on-board integrated circuitry, which further lowers the size and cost of the final sensing array structure.

Although less preferred in the broad practice of the present invention, relative to other forms of the gas sensor assembly illustratively described herein, the gas sensor assembly of the invention may be fabricated as a micro-hotplate sensor assembly, in which the gas sensing element is deployed with a protective coating over the active fluoro species sensing material.

Examples of illustrative film materials that may be employed for detection of fluoro species include Cr, Cu, W, Ni, Al, and Si, as useful metal species, as well as polymeric materials. Such sensing elements may be used in a chemical vapor deposition (CVD) process wherein nitrogen trifluoride ($NF_3$) is dissociated by a plasma to form reactive fluorine species.

$F_2$ or F reaching the MEMS sensor device reacts with the aluminum, nickel, tungsten, chrome, silicon or other active sensor material, resulting in a change in resistance of the material. This change in resistance will be a function of time, the operating temperature of the sensor material and the concentration of the fluorine-containing compound or ionic species.

In a reversible device, the fluorinated reaction product, such as $NF_2$, would remain on the sensing material, but the resistance of the material would increase in proportion to the thickness of the fluorinated film layer. When the target fluorinated compound is removed from the gas stream being monitored, the reaction at the surface of the active layer will be driven towards the metal. The initial resistance will thereby be recovered when the fluorine has been driven off.

In an irreversible process, the fluorinated reaction product, such as tungsten hexafluoride, $WF_6$, will volatilize and be removed in the gas stream. The resistance of the active layer will increase as the tungsten is removed. The resistance will not decrease upon removal of the fluorinated compounds. The rate of removal/resistance increase will be indicative of the amount of fluorinated species present. In this circumstance, it may be advantageous to provide several devices in an array, and to employ same sequentially, since they are consumed in the sensing process. A polymer or other organic film can effectively coat the unused sensing elements, and can be melted or burned off, as required in the operation of the device.

In the case of organic coatings as sensing materials, a wide variety of conductive polymers are commercially available. Examples of such polymers include, without limitation, polyphenylene vinylene, a cross linkable monomer cast from methanol, and octylthiophene, a well-characterized and readily commercially available material.

In general, gas is desorbed from polymers more slowly than it is adsorbed. Accordingly, adsorption/desorption schemes are enhanced by the ability of the micro-hotplate to ramp up the substrate temperature quickly, to aid in effecting rapid desorption of adsorbed gaseous species.

Adsorption of acidic species enhances the conductivity of conductive polymers by several orders of magnitude. Adsorption of species such as hydrogen chloride, which is present during an oxide chamber clean in a semiconductor manufacturing operation, will affect the conductivity of a polymer such as octylthiophene. Since HF is the reaction product of atomic fluorine with hydrogen found in the oxide, hydrogen fluoride may also be used as an indicator of the progress of the chamber clean process. The polymer conductivity may correspondingly remain constant or reverse as the level of hydrogen fluoride decreases, indicating the termination of the chamber clean process.

Alternatively, the sensing film, e.g., formed of octylthiophene, may react with fluorine present during the oxide chamber clean, causing a drastic reduction in the conductive properties of the polymer as the chemistry is changed by reaction of the polymer with fluorine.

It will be recognized that micro-hotplate embodiments of the gas sensing assembly of the present invention may be widely varied in respect of the component sensing films and reactive/sorptive chemistries employed, as determinable within the skill of the art for a given end use application of target gas species detection. Micro-hotplate detectors of a type adaptable to the practice of the present invention may be fabricated as more fully described in U.S. Pat. No. 6,265,222 issued Jul. 24, 2001 in the names of Frank DiMeo, Jr. and Gautam Bahndari, the disclosure of which hereby is incorporated herein by reference in its entirety.

In one presently preferred sensing element embodiment, wherein the sensing element is in the form of a filament, the sensor filament comprises a Monel core, e.g., having a diameter on the order of about 100 microns, which is nickel-plated. In lieu of Monel, other core materials, such as iron-nickel alloys, stainless steels, indium, vanadium and cobalt alloys, etc., may be employed for such composite wire sensor element.

Nickel is highly resistive in character, and Monel has an even higher resistivity. Their combination therefore enables maximization of the sensing signal with a large resistance, so that higher responsivity and effective signal generation are achieved.

In such core and cladding composite filament structures, the core material may comprise a material that would not itself be suitable as a sensor element, e.g., due to alloy contaminants or other considerations, but which has a high resistivity that enables another material, such as nickel, when plated thereon, to compensate for the deficiencies of the core material, and provide an overall high signal, high resistivity composite sensor element.

The details, features, and embodiments of the invention are more fully illustrated with respect to the following non-limiting examples.

Example 1

A platinum foil having a thickness of 4 micrometers ($\mu m$) was connected via spot welding to the four contacts of an 8-lead TO-5 header. Laser micro-machining was used to form a narrow, higher resistance area, with an approximate size of 80 $\mu m \times 50$ $\mu m$. The room temperature (~25° C.) resistance of the foil between the middle two contacts was 0.14$\Omega$. This foil, as reconfigured to a filament form, was the Pt test sample.

Figure 26:
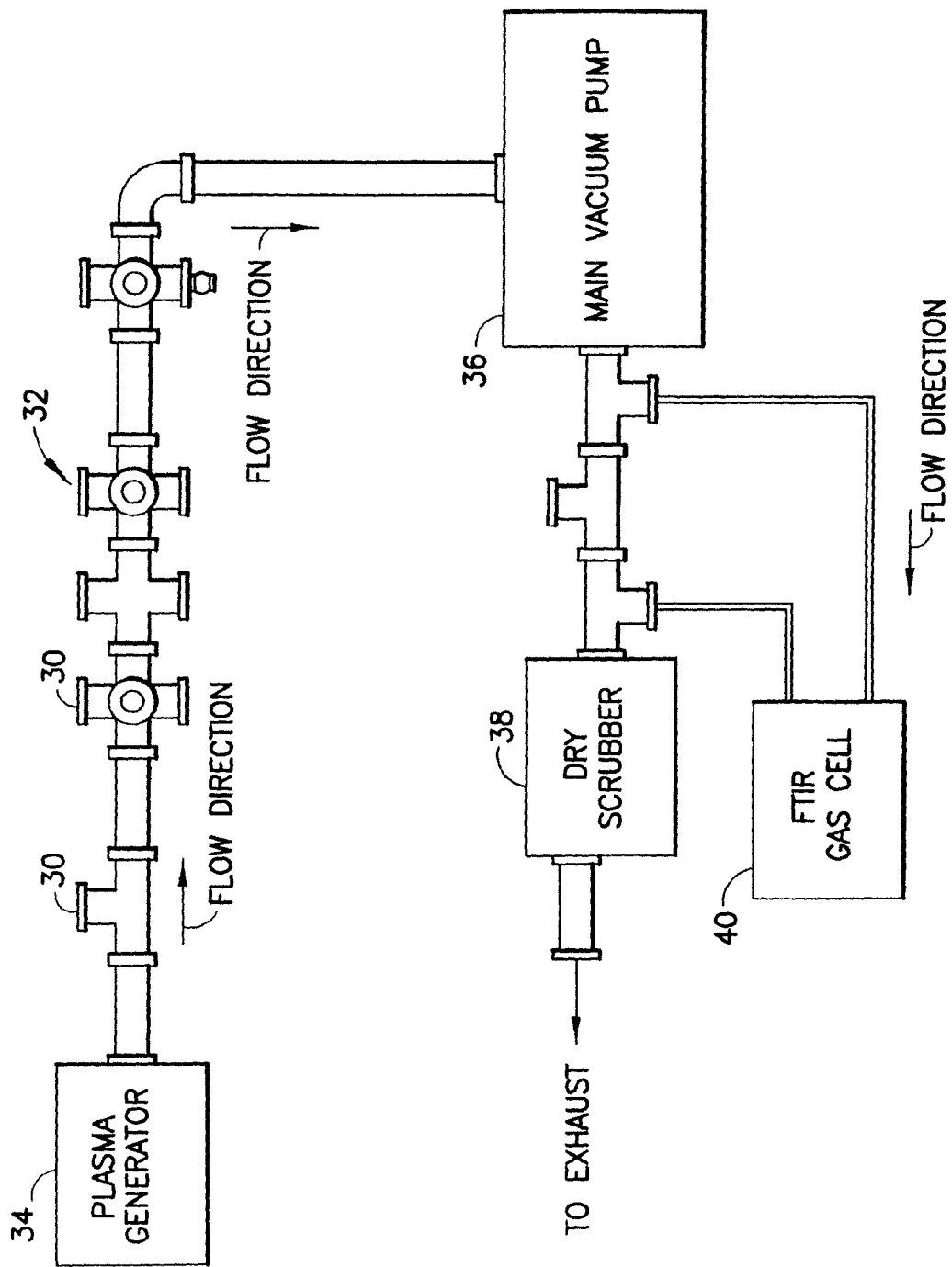
FIG. 26 is a schematic diagram of an $NF_3$ plasma test manifold.

The $NF_3$ plasma test manifold used in this test is illustrated schematically in FIG. 26, as including silicon wafers 30 in the manifold flow circuitry (which however were provided in the flow circuit only in the semiconductor chamber clean process simulation test and not in the baseline run), upstream of the Pt test sample 32.

The manifold flow circuitry included a flow conduit joining the plasma generator 34 with a downstream main vacuum pump 36, which in turn was joined to a dry scrubber unit 38. The distance from the juncture of the plasma generator 34 with the manifold conduit to the Pt test sample 32 was 28 inches. The manifold conduit between the main vacuum pump 36 and the dry scrubber 38 was equipped with taps to which an FTIR gas cell 20 was coupled, via associated gas flow tubing, as shown. The direction of flow in the test manifold is shown at respective positions in the flow circuit by arrows labeled "flow direction."

A free-standing Pt foil was installed in the $NF_3$ plasma test manifold illustrated in FIG. 26, and exposed to various fluorinated species. The plasma test was conducted at a pressure of about 5 torr. A constant current (I) of 50 mA was run through the foil and the voltage change ($\Delta V$) measured as a function of time. The $SiF_4$ concentration was measured downstream of the main vacuum pump 36, using the FTIR gas cell 40, also as a function of time.

Figure 27:
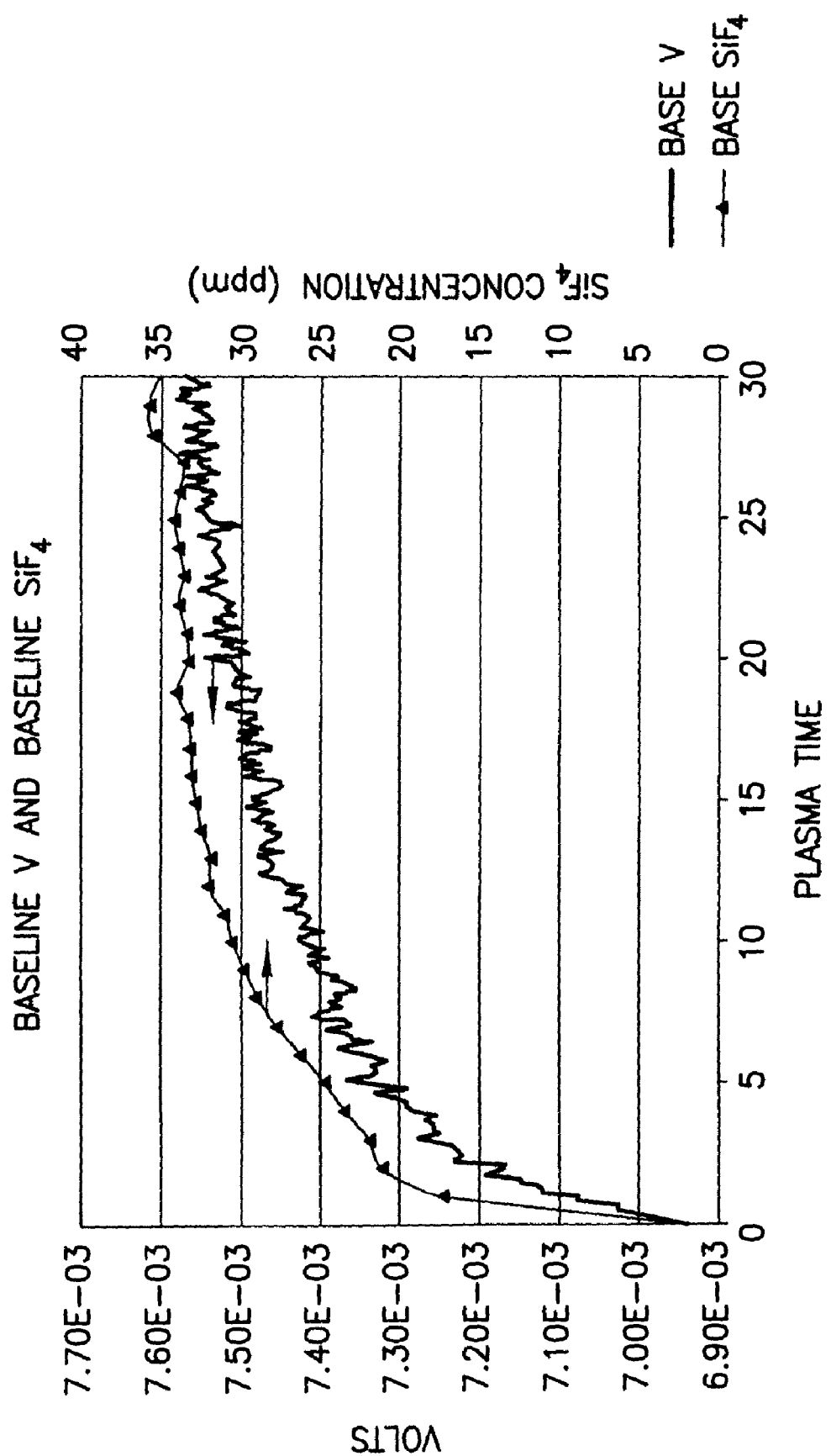
FIG. 27 is a graph of voltage drop and $SiF_4$ concentration from Fourier Transform Infrared (FTIR) monitoring of a baseline Pt foil test.

When the foil was exposed to the baseline condition (without Si or $SiO_2$ present), the voltage drop in the foil increased in a manner similar to the $SiF_4$ concentration, as shown in FIG. 27.

$NF_3$ plasma was generated by the plasma generator 34 and flowed into the manifold in the baseline test as well as in the subsequent chamber clean process simulation test. $NF_3$ plasma is known to attack silicon and $SiO_2$ that may be present on the sidewalls of a semiconductor processing chamber. The by-product of the $NF_3$ plasma includes volatile $SiF_4$. When the chamber is clean, the concentration of $SiF_4$ decreases. To simulate this occurrence in the test manifold, silicon wafers 30 were provided in the manifold to generate $SiF_4$.

Figure 28:
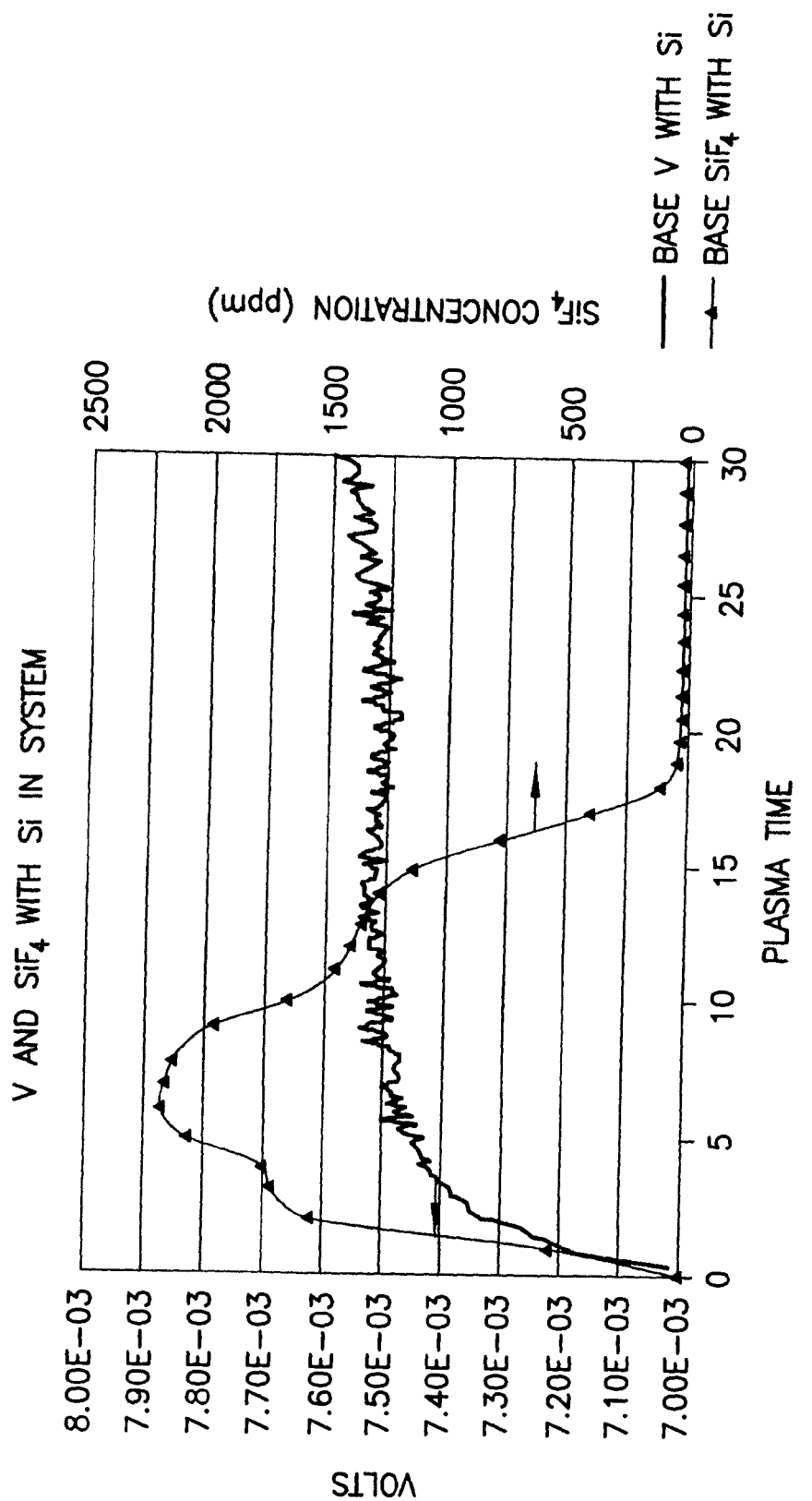
FIG. 28 is a graph of voltage drop and $SiF_4$ concentration from FTIR monitoring of the Pt foil when a silicon chip was added.

The voltage drop across the exposed Pt foil element as a function of time, and the $SiF_4$ concentration as a function of time, with Si present, are shown in FIG. 28.

Figure 29:
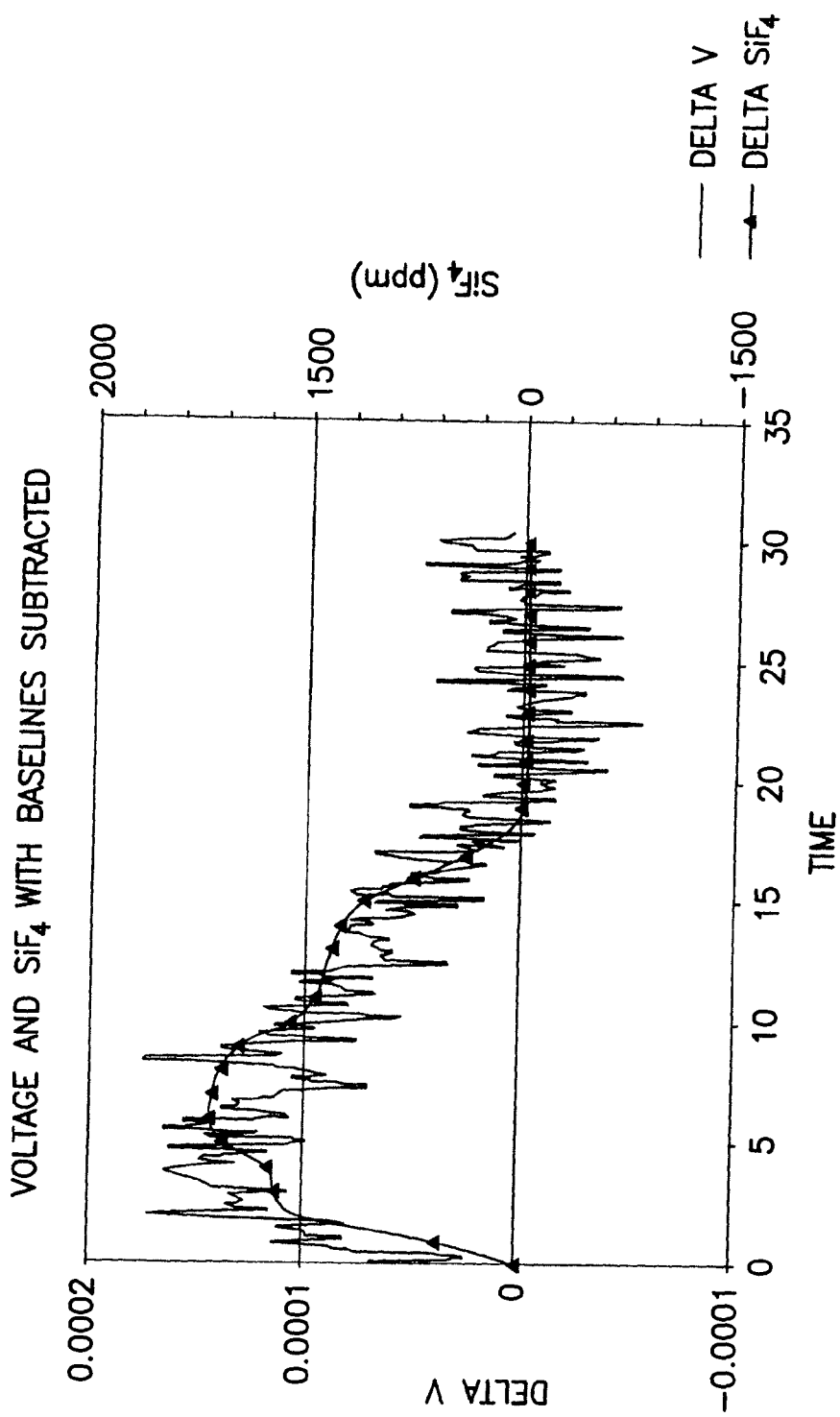
FIG. 29 is a graph of both the $SiF_4$ concentration and the change in Pt resistance, as a function of time, with the $SiF_4$ concentration measured using an FTIR on the exhaust line.

FIG. 29 shows the difference in voltage drop between the baseline experiment and the experiment with silicon. The increase in voltage drop correlated extremely well with the increase in $SiF_4$ generated, and the reaction appeared to be reversible, with the Pt resistance returning to the pre-exposure value. The resistance increase in the Pt foil was much greater than that calculated based on the known temperature coefficient of resistivity; consequently, this increase in resistance was attributed to a chemical interaction between the $NF_3$ plasma, Si effluents and the Pt foil.

Example 2

To demonstrate the use of three-dimensional architectures, three prototype sensors were constructed of machined VESPEL® polyimide as shown in FIGS. 30-35.

Figure 30:
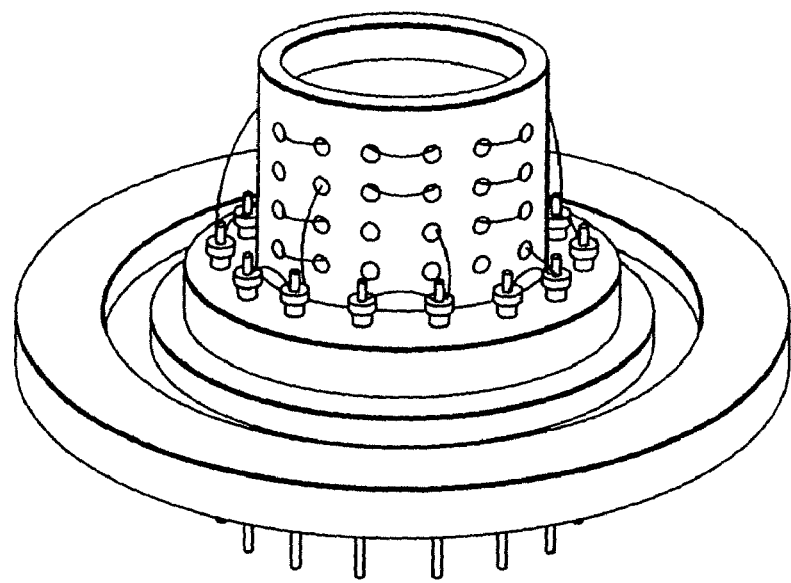
FIG. 30 is a side view of a machined VESPEL® polyimide sensor assembly according to another embodiment of the invention.
Figure 31:
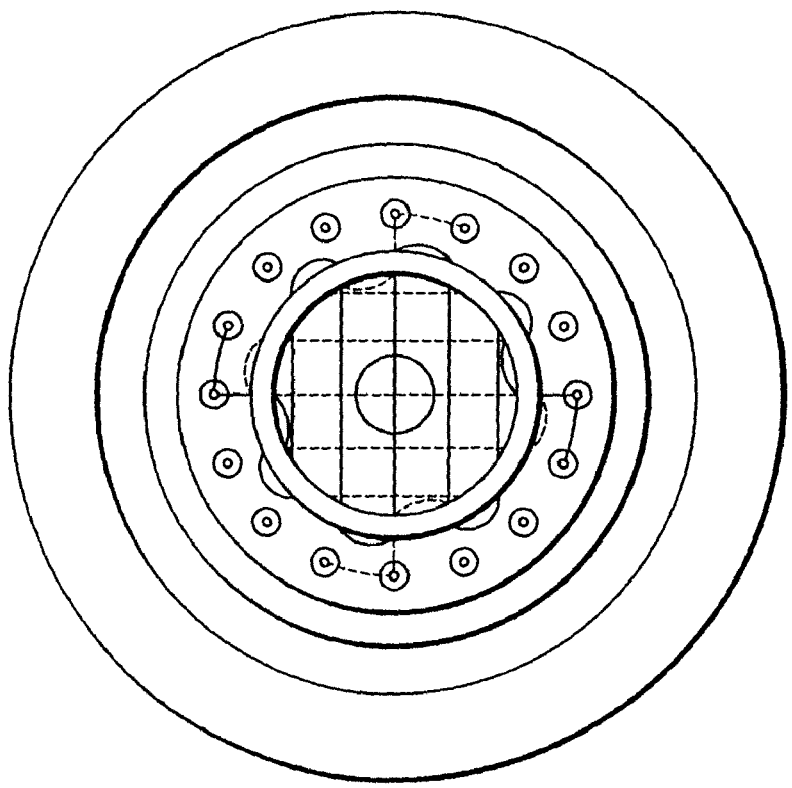
FIG. 31 is a top view of the sensor array of FIG. 30.

FIGS. 30 and 31 show respectively a side view (FIG. 30) and a top view (FIG. 31) of a machined VESPEL® polyimide sensor array utilizing a cylindrical pegboard design mounted on an aluminum flange, wherein each sensing wire has four-point contact via press-fitted posts.

Figure 32:
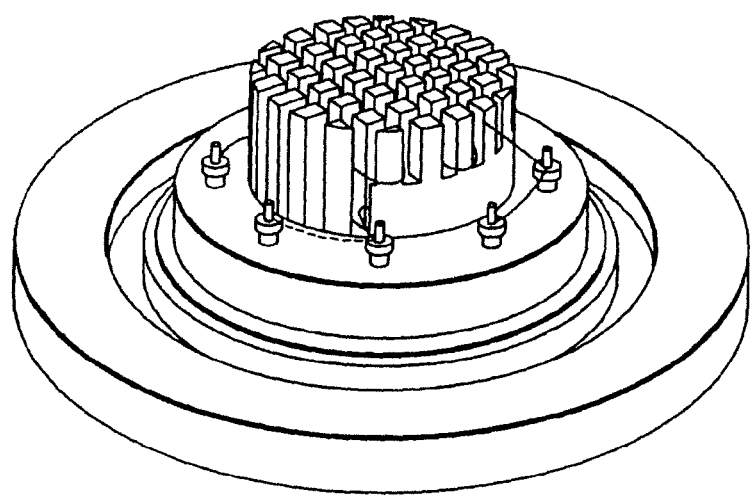
FIG. 32 is a side view of a machined VESPEL® polyimide sensor assembly, according to yet another embodiment of the invention.
Figure 33:
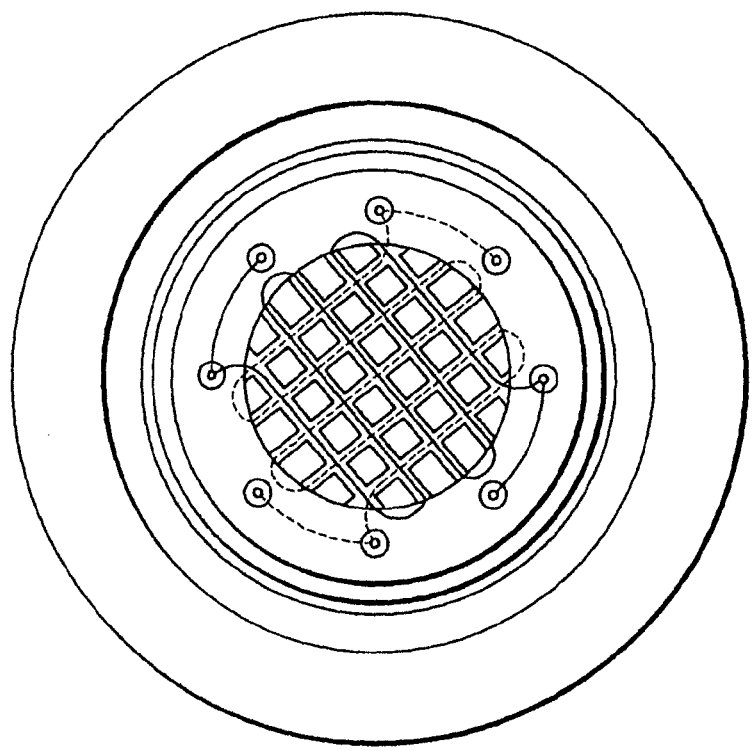
FIG. 33 is a top view of the sensor assembly of FIG. 34.

FIGS. 32 and 33 show respectively a side view (FIG. 32) and a top view (FIG. 33) of a machined VESPEL® polyimide sensor assembly utilizing an orthogonally-cut VESPEL® polyimide post and channels design (with shelves) mounted on an aluminum flange, wherein each sensing wire has four-point electrical contact via press-fitted posts.

Figure 34:
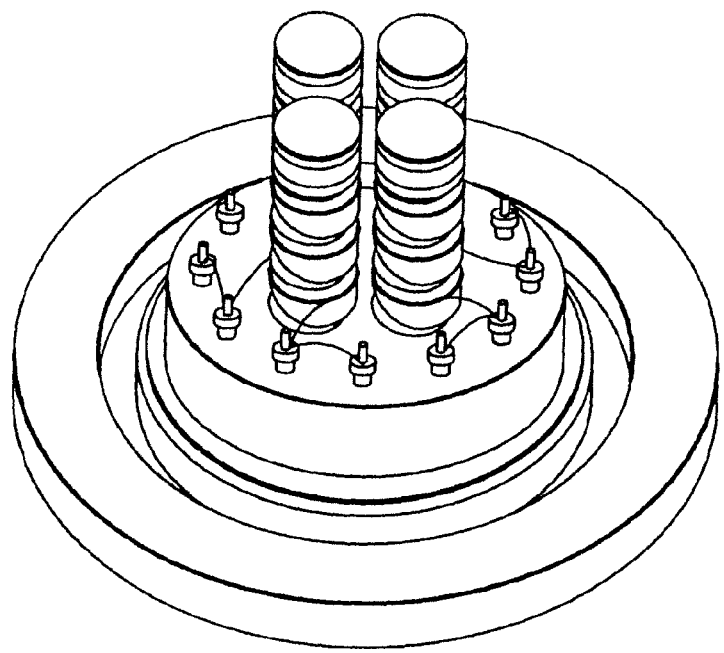
FIG. 34 is a side view of a machined VESPEL® polyimide sensor assembly according to a further embodiment of the invention.
Figure 35:
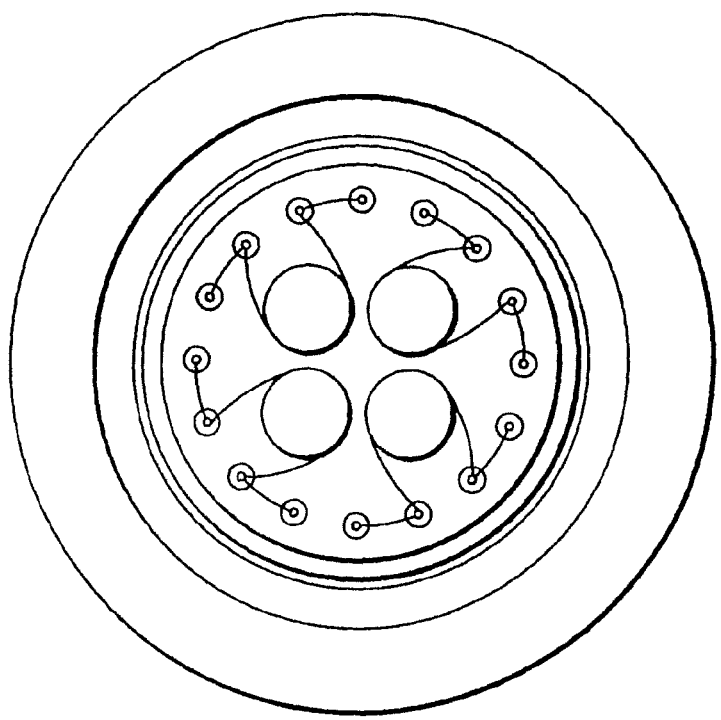
FIG. 35 is a top view of the sensor assembly of FIG. 34.

FIGS. 34 and 35 show respectively a side view (FIG. 34) and a top view (FIG. 35) of a machined VESPEL® polyimide sensor assembly mounted on an aluminum flange, utilizing VESPEL® polyimide cylinders with spiraling grooves of varying lengths allowing a single sensing wire to be woven "up" and "down" the length of a single VESPEL® polyimide cylinder. Multiple cylinders allow the use of multiple sensing wires, wherein each sensing wire has four-point electrical contact via press-fitted posts.

The sensor of FIGS. 30-31 was machined from a VESPEL® polyimide cylinder to replicate the non-planar pegboard structure hereinabove in FIG. 25. This prototype was constructed in a multiple sensing array, utilizing platinum, nickel, copper and aluminum wires in a 16-pin, four-point electrical contact per wire format.

The sensor shown in FIGS. 32-33 was machined to replicate the orthogonally-cut VESPEL® polyimide structure with channels, posts and shelves illustrated in FIG. 20. This prototype was constructed in a multiple-sensing array utilizing copper and aluminum wires in an 8-pin, four-point electrical contact per wire format.

The sensor of FIGS. 34-35 represents a variation on the channels and shelves design. The channels in this prototype were cut in a spiral pattern along the length of a single cylindrical VESPEL® polyimide post, and the sensing wire was woven inside the channel. By cutting two separate spiral channels of different depths, which criss-cross one another along the length of the VESPEL® polyimide post, the sensing wire can be made to make two passes along the length of the post, being woven up the post in one groove and down the post in a second groove. Because the posts have different depths, the wire does not contact itself as it passes itself in the groove intersections. This prototype was constructed in a multiple sensing metal array, utilizing platinum, nickel, copper and aluminum wires in a 16-pin, four-point electrical contact per wire format.

Example 3

In this example, data was generated in the course of a 100 wafer run. A gas sensor assembly was constructed using a cylindrical pegboard member providing a scaffolding support structure for a nickel sensing wire and a copper sensing wire. The copper wire was positioned at an upper portion of the cylinder, and the nickel sensing wire was positioned at a lower portion of the cylinder. A 75 milliamp constant DC current was passed through the nickel wire and the copper wire in series.

Each of the nickel and copper wires was nominally 100 microns in diameter and approximately 13-14 centimeters in length. The electrical resistance of the nickel wire was ~1.3 ohms, and the resistance of the copper wire was ~0.255 ohms.

Gaseous effluent from a process chamber undergoing successive deposition and chamber clean operations was contacted with the sensing wires and the rate of change of the resistivity of the gas sensing wires was monitored as a function of time during both the deposition step and the chamber clean step.

Figure 36:
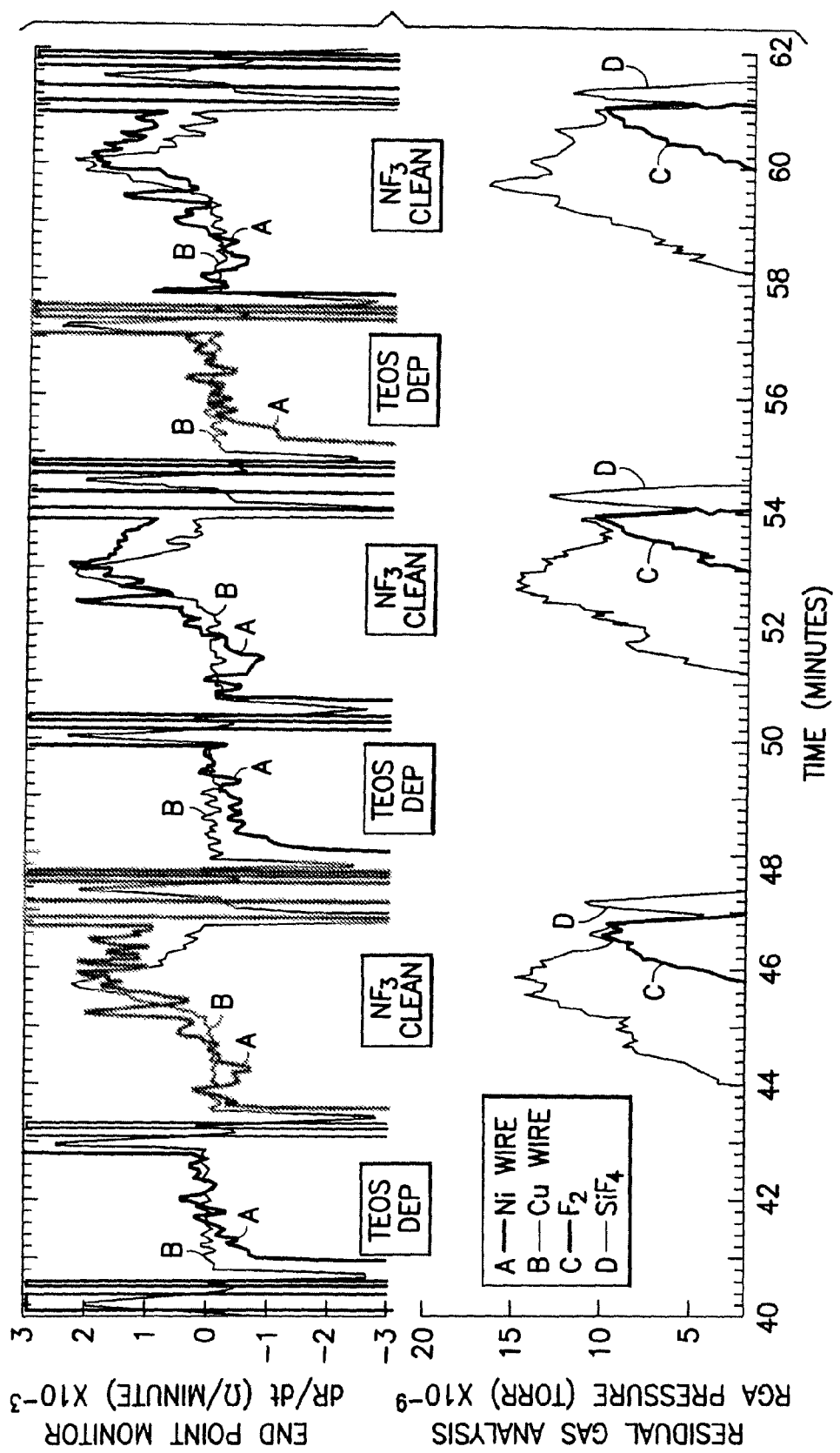
FIG. 36 is a graph of end point monitor behavior, for a gas sensing assembly constructed in accordance with a still further embodiment of the invention, shown in the upper portion of the graph, and residual gas analyzer concentration, shown in the lower portion of the graph, as a function of time, in minutes.

The deposition step involved deposition of silicon on a substrate from a tetraethylorthosilicate (TEOS) source reagent, followed by the cleaning of the chamber with $NF_3$. In order to correlate the dynamic resistivity behavior of the gas sensing wires with the process operation, effluent gas from the chamber after contacting with the gas sensing assembly was passed through a residual gas analyzer (RGA) unit. The output of the RGA unit was monitored as a function of time, and the graphical outputs of the gas sensing assembly and the RGA unit were superposed as a function of time, as shown in the graph of FIG. 36.

The process conditions that were employed in the constituent deposition and clean steps are set out below.

TEOS Deposition
Chamber Pressure=9 Torr
Chamber Temp=390° C.
RF Power=350 Watts
TEOS Flow Rate=230 sccm
Helium Flow Rate 100 sccm
Oxygen Flow Rate 220 sccm Each TEOS deposition was 120 seconds in duration.

$NF_3$ Clean Operation
Chamber Pressure=3.2 Torr
Chamber Temperature=390° C.
RF Power=350 Watts
Helium Flow Rate=225 sccm
$NF_3$ Flow Rate=100 sccm Each $NF_3$ clean cycle was 200 seconds in duration.

FIG. 36 is a graph of the behavior of the gas sensing assembly as an end point monitor (EPM), shown in the upper portion of the graph, and residual gas analyzer (RGA) gas concentration, shown in the lower portion of the graph, as a function of time, in minutes.

Curves A and B show the change in resistance, in units of (ohms/minute)$\times 10^{-3}$, as a function of time, for successive tetraethylorthosilicate (TEOS) deposition steps and alternating nitrogen trifluoride ($NF_3$) cleaning steps in the previously described process operation.

The lower portion of FIG. 36 shows the residual gas analyzer monitored concentrations of fluorine (Curve C) and silicon tetrafluoride (Curve D) as a function of time, in minutes.

It is apparent from the superposition of the upper and lower portions of the graph in FIG. 36 that the resistance change of the end point monitor sensing element (wire) in the test correlated well with the fluoro species detection by the residual gas analyzer, showing that the gas sensing assembly provided a highly effective means of monitoring fluoro species in the chamber clean operations.

Although the invention has been variously described herein with reference to illustrative embodiments and features, it will be appreciated that the embodiments and features described hereinabove are not intended to limit the invention, and that other variations, modifications and other embodiments will readily suggest themselves to those of ordinary skill in the art, based on the disclosure herein. The invention therefore is to be broadly construed, consistent with the claims hereafter set forth.

What is claimed is:
1. A gas sensor device comprising:
first and second metal-containing posts;
at least one nickel-containing metal sensor wire supported between said first and second metal-containing posts to provide a gas sensing structure adapted for contacting gas susceptible to presence of one or more target species therein with which the at least one nickel-containing metal sensor wire is interactive to produce a response indicative of the presence of said one or more target species;

a polymeric block element intermediately arranged between ends of the first metal-containing post and ends of the second metal-containing post, with the first and second metal-containing posts extending through the polymeric block element; and a base including a proximal surface, wherein the at least one nickel-containing metal sensor wire is orthogonally arranged relative to the proximal surface, and the base comprises a KF flange.

2. The gas sensor device of claim 1, wherein the at least one nickel-containing metal sensor wire is bonded at anchoring points to said first and second posts.

3. The gas sensor device of claim 1, wherein at least an outer surface of the at least one nickel-containing metal sensor wire consists of nickel.

4. The gas sensor device of claim 1, operatively arranged to sense one or more target gas species in or downstream of a process chamber used for manufacture of semiconductor devices.

5. The gas sensor device of claim 1, wherein the polymeric block element comprises polyimide.

6. The gas sensor device of claim 1, further comprising a monitoring element operatively coupled with the at least on nickel-containing metal sensor wire and adapted to generate a signal that varies in relation to concentration of said target species sensed by the at least one nickel-containing metal sensor wire.

7. A method of monitoring a fluid locus for the presence or change in concentration of at least one target species therein utilizing the gas sensor device of claim 1, said method comprising:

(a) exposing fluid from said fluid locus to the at least one nickel-containing metal sensor wire;

(b) monitoring said at least one property of the at least one nickel-containing metal sensor wire during step (a); and (c) responsively generating an output signal when the at least one nickel-containing metal sensor wire exhibits said change in at least one property of the at least one nickel-containing metal sensor wire, indicating the presence or change in concentration of a target species in the fluid locus.

8. The method of claim 7, wherein the fluid locus is disposed in or downstream of a process chamber used for manufacture of semiconductor devices.

9. The method of claim 8, wherein the fluid locus comprises a fluid stream in a processing facility adapted to manufacture semiconductor devices.

10. The method of claim 8, wherein at least an exterior surface of the at least one nickel-containing metal sensor wire consists of nickel.

11. The method of claim 8, wherein the output signal generated in step (c) is employed for one of the following: to control a process in which the target species is generated, to control one or more valves, or to effect an operational change in a process having the target species generated as a chemical reaction product.

12. The method of claim 8, wherein the gas sensor device is used to monitor etch effluent species during chamber cleaning, and the output signal is used to determine end-point of chamber cleaning.

13. The method of claim 8, wherein the gas sensor device is adapted to exhibit a change in at least one property thereof upon contact with target species comprising at least one of $NF_3$, $SiF_4$, $C_2F_6$, HF, $F_2$, $COF_2$, $ClF_3$, $IF_3$, chamber etch gases, and etch by-products.

14. A gas sensor device adapted to detect target species in a gas environment, the gas sensor device including:

a sensing element comprising a sensing wire supported by a plurality of metal posts sheathed with an insulating material at all areas except at points of electrical contact with the sensing wire, wherein the sensing wire has at least an outer surface comprising nickel or nickel alloy, is adapted to contact the gas environment, is adapted to interact with said target species in said gas environment, and is adapted to responsively exhibit a monitorable change upon exposure to said target species, said monitorable change being correlative of concentration of said target species; and a monitoring element operatively coupled with the sensing element and adapted to generate a signal that varies in relation to concentration of said target species sensed by the sensing element.

15. The gas sensor device of claim 14, operatively arranged to sense one or more target gas species in or downstream of a process chamber used for manufacture of semiconductor devices.

16. A method of monitoring a fluid locus for the presence or change in concentration of at least one target species therein utilizing the gas sensor device of claim 14, said method comprising:

(a) exposing fluid from said fluid locus to the sensing wire;

(b) monitoring said at least one property of the sensing wire during step (a); and (c) responsively generating an output signal when the sensing wire exhibits said monitorable change, indicating the presence or change in concentration of a target species in the fluid locus.

17. The method of claim 16, wherein the fluid locus is disposed in or downstream of a process chamber used for manufacture of semiconductor devices.

18. The method of claim 16, wherein the fluid locus comprises a fluid stream in a processing facility adapted to manufacture semiconductor devices.

19. The method of claim 16, wherein at least an exterior surface of the at least one nickel-containing metal sensor wire consists of nickel.

20. The method of claim 16, wherein the output signal generated in step (c) is employed for one of the following: to control a process in which the target species is generated, to control one or more valves, or to effect an operational change in a process having the target species generated as a chemical reaction product.

21. The method of claim 16, wherein the gas sensor device is used to monitor etch effluent species during chamber cleaning, and the output signal is used to determine end-point of chamber cleaning.

22. The method of claim 16, wherein the gas sensor device is adapted to exhibit a monitorable change upon exposure to target species comprising at least one of $NF_3$, $SiF_4$, $C_2F_6$, HF, $F_2$, $COF_2$, $ClF_3$, $IF_3$, chamber etch gases, and etch by-products.

* * * * *

UNITED STATES PATENT AND TRADEMARK OFFICE
CERTIFICATE OF CORRECTION

| | | |
|---|---|---|
| PATENT NO. | : 8,109,130 B2 | Page 1 of 1 |
| APPLICATION NO. | : 12/537910 | |
| DATED | : February 7, 2012 | |
| INVENTOR(S) | : Frank Dimeo et al. | |

It is certified that error appears in the above-identified patent and that said Letters Patent is hereby corrected as shown below:

Column 25, line 26: "...at least on..." should be -- at least one --.

Signed and Sealed this
Tenth Day of July, 2012

David J. Kappos
*Director of the United States Patent and Trademark Office*